United States Patent
Gunderson et al.

(10) Patent No.: US 11,634,707 B2
(45) Date of Patent: Apr. 25, 2023

(54) METHODS AND COMPOSITIONS FOR ANALYZING CELLULAR COMPONENTS

(71) Applicant: Illumina, Inc., San Diego, CA (US)

(72) Inventors: Kevin L Gunderson, Encinitas, CA (US); Frank J Steemers, Encinitas, CA (US); Jeffrey S Fisher, San Diego, CA (US); Roberto Rigatti, Essex (GB)

(73) Assignee: ILLUMINA, INC., San Diego, CA (US)

( * ) Notice: Subject to any disclaimer, the term of this patent is extended or adjusted under 35 U.S.C. 154(b) by 164 days.

(21) Appl. No.: 15/549,334

(22) PCT Filed: Feb. 10, 2016

(86) PCT No.: PCT/US2016/017391
§ 371 (c)(1),
(2) Date: Aug. 7, 2017

(87) PCT Pub. No.: WO2016/130704
PCT Pub. Date: Aug. 18, 2016

(65) Prior Publication Data
US 2018/0273933 A1    Sep. 27, 2018

Related U.S. Application Data

(60) Provisional application No. 62/114,505, filed on Feb. 10, 2015.

(51) Int. Cl.
*C12N 15/10*    (2006.01)
*C12Q 1/6869*    (2018.01)
*C12Q 1/6806*    (2018.01)

(52) U.S. Cl.
CPC ....... *C12N 15/1065* (2013.01); *C12Q 1/6806* (2013.01); *C12Q 1/6869* (2013.01)

(58) Field of Classification Search
CPC .............. C12N 15/1065; C12Q 1/6869; C12Q 2537/143; C12Q 2563/159; C12Q 2563/14
See application file for complete search history.

(56) References Cited

U.S. PATENT DOCUMENTS

| | | |
|---|---|---|
| 9,029,085 B2 | 5/2015 | Agresti et al. |
| 2005/0032126 A1 | 2/2005 | Coombs et al. |
| 2009/0081688 A1 | 3/2009 | Luo et al. |
| 2012/0135394 A1 | 5/2012 | Kim et al. |
| 2012/0208724 A1 | 5/2012 | Steemers |
| 2012/0208705 A1 | 8/2012 | Steemers |
| 2012/0220494 A1* | 8/2012 | Samuels ............ C12N 15/1075 506/16 |
| 2013/0023433 A1 | 1/2013 | Luo et al. |
| 2013/0203605 A1* | 8/2013 | Shendure ............ C12N 15/1093 506/2 |
| 2014/0228255 A1* | 8/2014 | Hindson ............ C12N 15/1065 506/26 |

FOREIGN PATENT DOCUMENTS

| | | | |
|---|---|---|---|
| RU | 2532853 | 11/2014 | |
| WO | WO-2011106314 A2 * | 9/2011 | ............. C40B 50/06 |
| WO | 2012061832 | 5/2012 | |
| WO | WO-2012061832 A1 * | 5/2012 | ......... C12N 15/1093 |
| WO | WO-2012106385 A2 * | 8/2012 | ............. C12Q 1/686 |
| WO | WO-2013078470 A2 * | 5/2013 | ....... C12Q 2522/101 |
| WO | 2014-028378 | 2/2014 | |
| WO | 2014/142850 A1 | 9/2014 | |
| WO | 2012048341 | 4/2016 | |

OTHER PUBLICATIONS

Fan et al., "Combinatorial labeling of single cells for gene expression cytometry", Science, vol. 347, No. 6222, Feb. 6, 2015, 1258367: 1-8.
Fredriksson et al., "Protein detection using proximity-dependent DNA ligation assays", Nat. Biotechnol, vol. 20, No. 5, May 1, 2002, 473-477.
Lohr et al., "Whole exome sequencing of CTCs as a window into metastatic cancer", Nat Biotechnol, vol. 32, No. 5, Apr. 20, 2014, 479-484.
Nakazawa et al., "RNA sequencing of circulating tumor cells from men with castration-resistant prostate cancer", J. Urology, vol. 191, No. 4S Supplement, Apr. 1, 2014, p. e583: MP52-10.
Stahlberg et al., "Quantitative PCR Analysis of DNA, RNAs, and Proteins in the Same Single Cell", Clin Chem, vol. 58, No. 12, Sep. 26, 2012, 1682-1691.
Supplementary Search Report, Singapore Patent Application No. 11201706504R, dated Mar. 12, 2019, 3 pages.
Islam et al., "Quantitative single-cell RNA-seq with unique molecular identifies" 2014 *Nature Methods*, 11(2):163.
Ivanov et al., "Typing of mitochondrial DNA in individual cells of human buccal epithelium" 2011 *Forensic Medical Examination*, 54(5):30-33.
Amini, Sasan et al., "Haplotype-resolved whole-genome sequencing by contiguity-preserving transposition and combinatorial indexing", Nature Genetics, vol. 46 No. 12, Dec. 2014, 1343-1349.
Mizuuchi, Kiyoshi, "Transpositional Recombination: Mechanistic Insights from Studies of Mu and Other Elements", Annu. Rev. Biochem. 61, 1992, 1011-51.
Wezyk, Magdalena, Authorized Officer, ISA/EPO, International Search Report and Written Opinion, International Patent Application No. PCT/US2016/017391, dated Aug. 9, 2016, 23 pages.

(Continued)

*Primary Examiner* — Sahana S Kaup
(74) *Attorney, Agent, or Firm* — Mueting Raasch Group

(57) ABSTRACT

Embodiments of the present invention relate to analyzing components of a cell. In some embodiments, the present invention relate to analyzing components of a single cell. In some embodiments, the methods and compositions relate to sequencing nucleic acids. In some embodiments, the methods and compositions relate to identifying and/or quantitating nucleic acid, proteins, organelles, and/or cellular metabolites.

23 Claims, 16 Drawing Sheets
Specification includes a Sequence Listing.

(56) References Cited

OTHER PUBLICATIONS

Adey, A. et al., "In vitro, long-range sequence information for de novo genome assembly via transposase contiguity," Genome Res. 2014, 24(12), 2041-2049.
Cusanovich, D. et al., "Multiplex single-cell profiling of chromatin accessibility by combinatorial cellular indexing," Science 2015, 348(6237), 910-914.
Russian Office Action for RU Application No. 2020110764 issued by the Federal Institute of Industrial Property on Apr. 21, 2021; 11 pgs. including English Translation.
Arnaud, "Microfluidic Devices Capture Tumor Cells," Apr. 15, 2013, *Analytical Chemistry*, 91(15): 4 pages.
Hashimshony et al., "CEL-Seq: Single-Cell RNA-Seq by Multiplexed Linear Amplification," Sep. 27, 2012, *Cell Reports*, 2:666-73.

\* cited by examiner

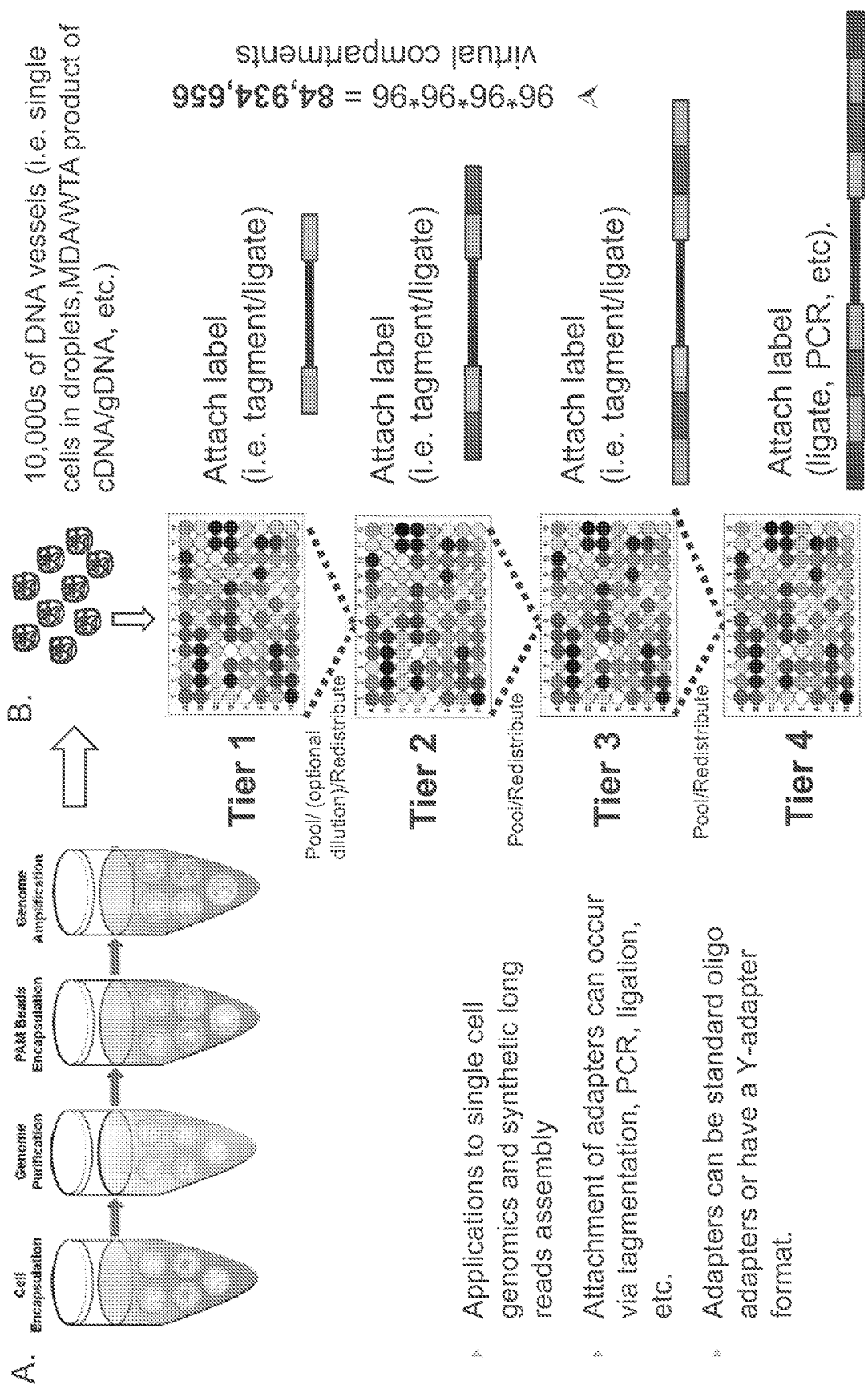

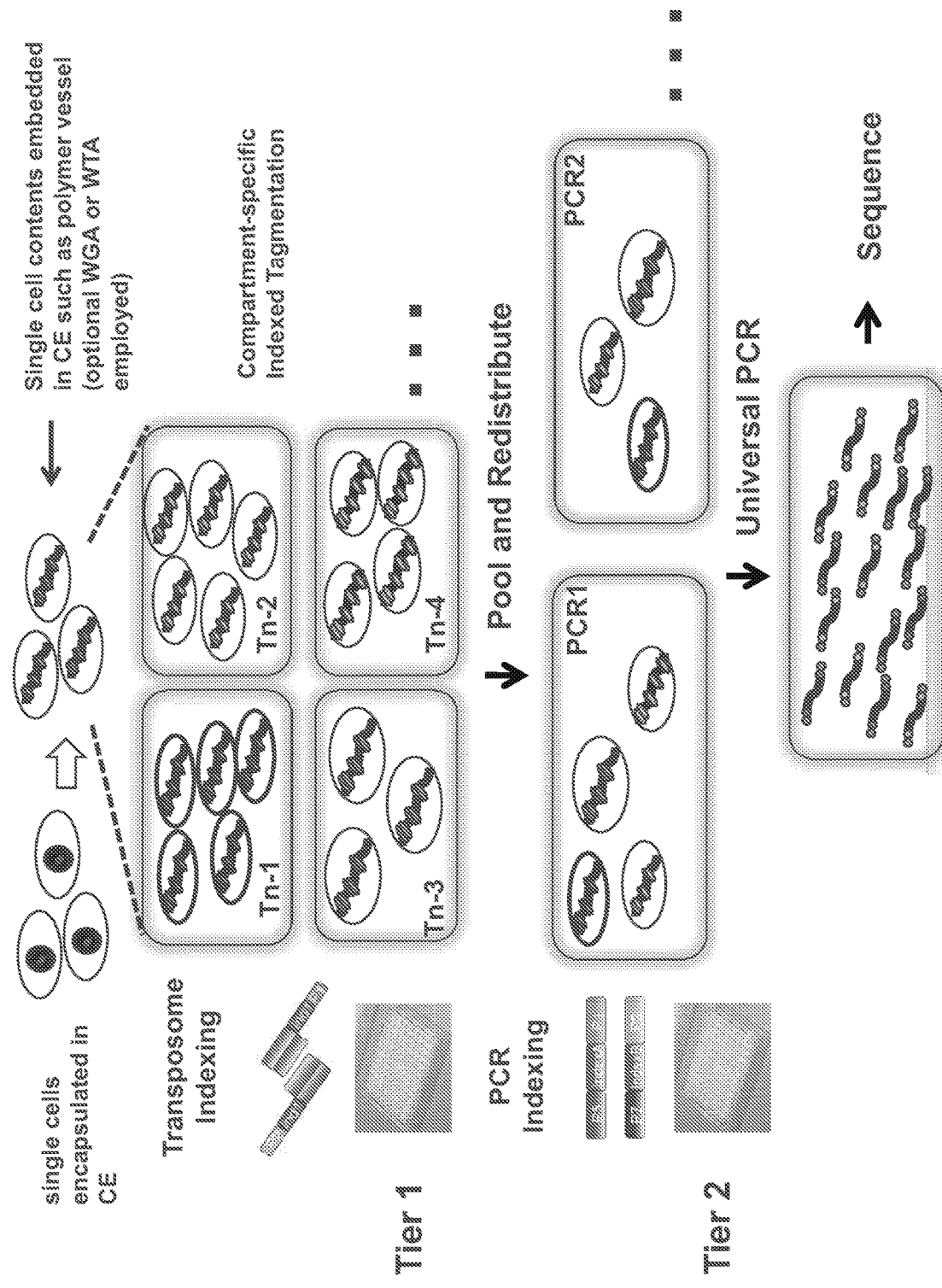

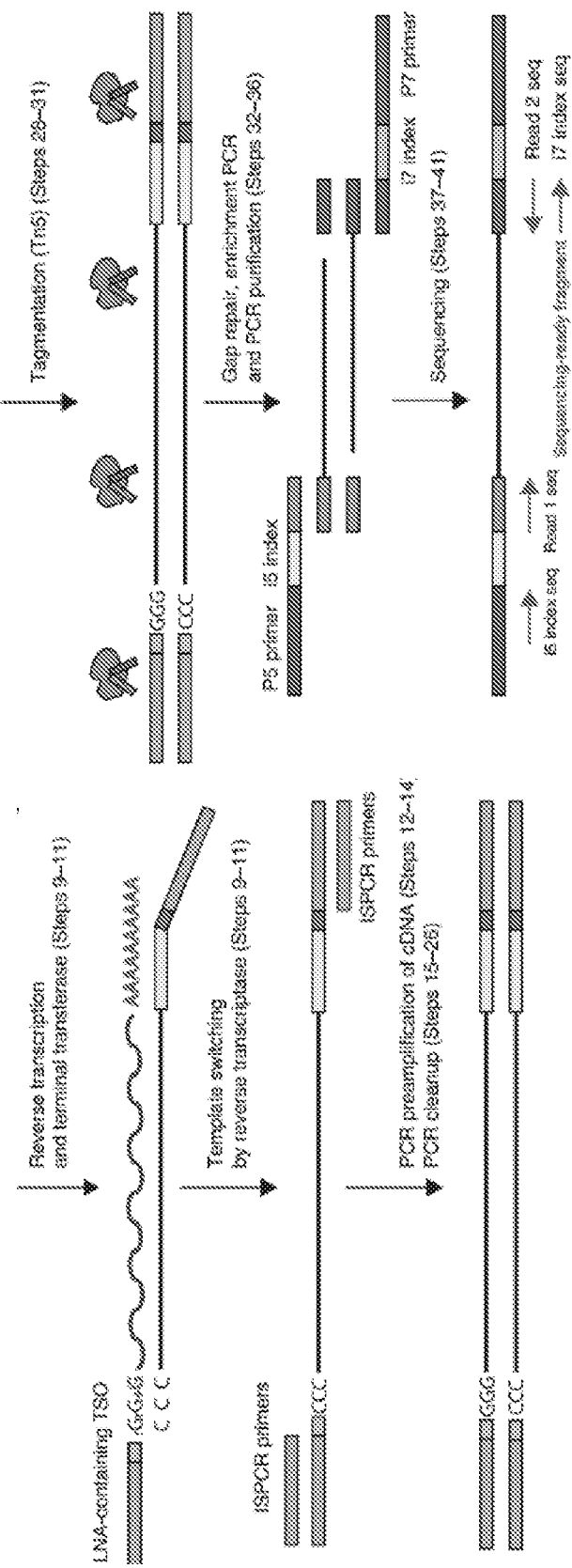

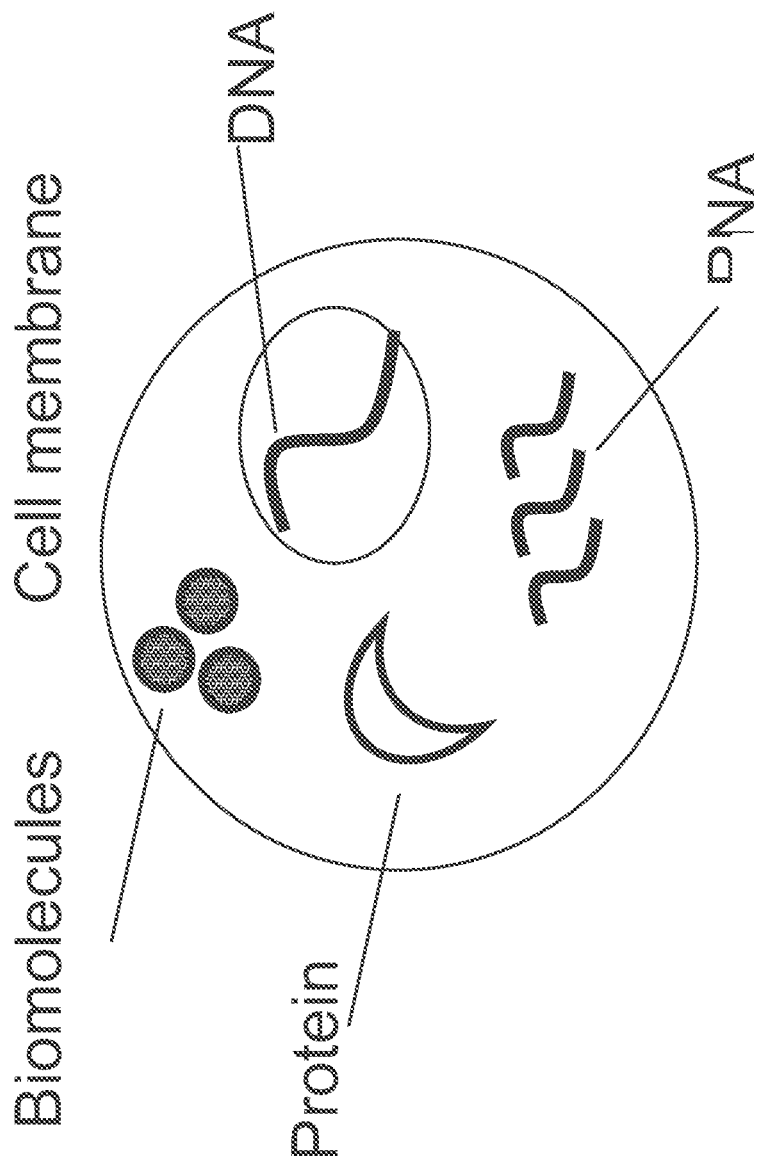
Fig. 4: Single cell contents in a vessel
Cross-section of a cell showing the various biomolecules

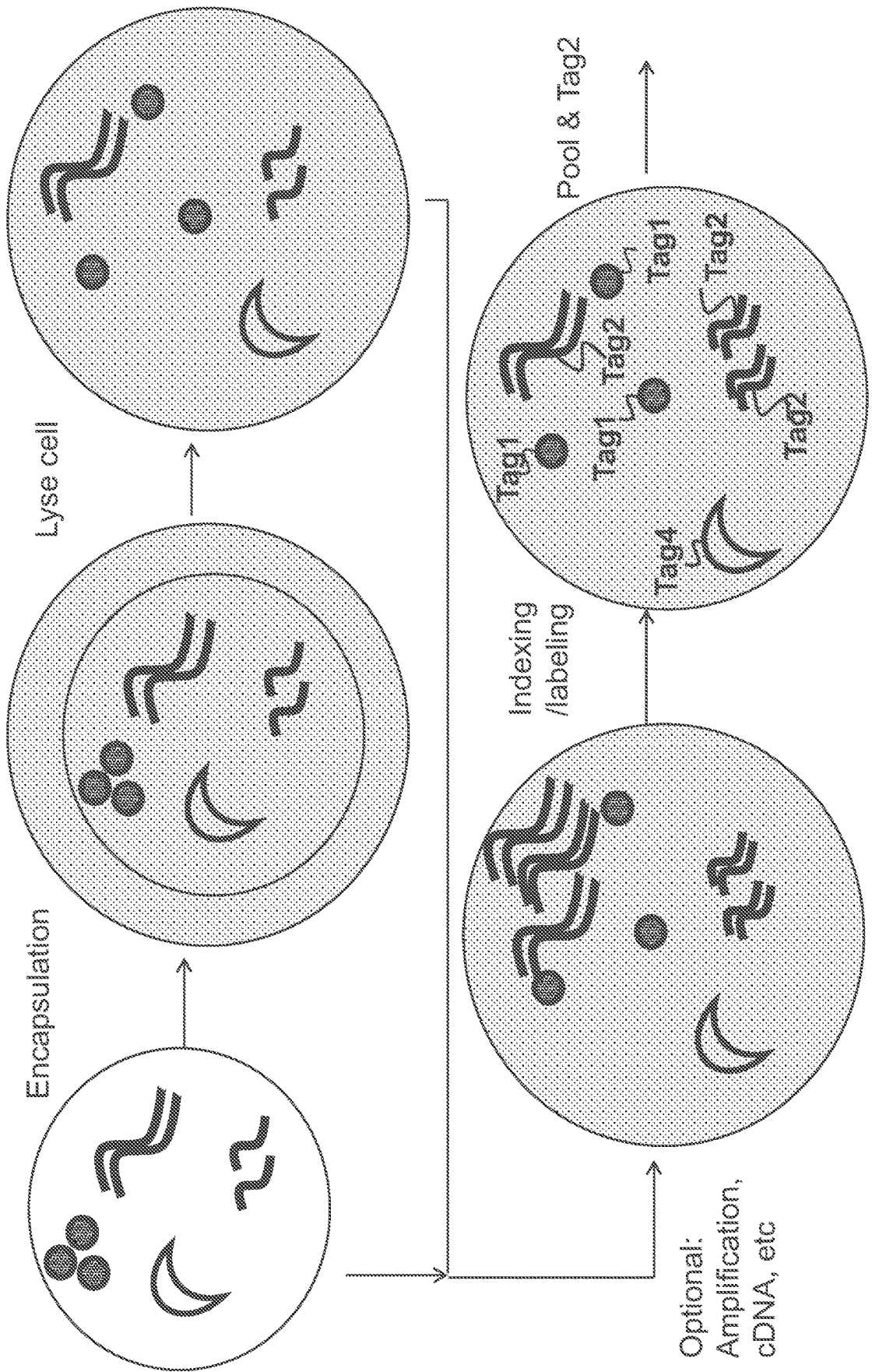

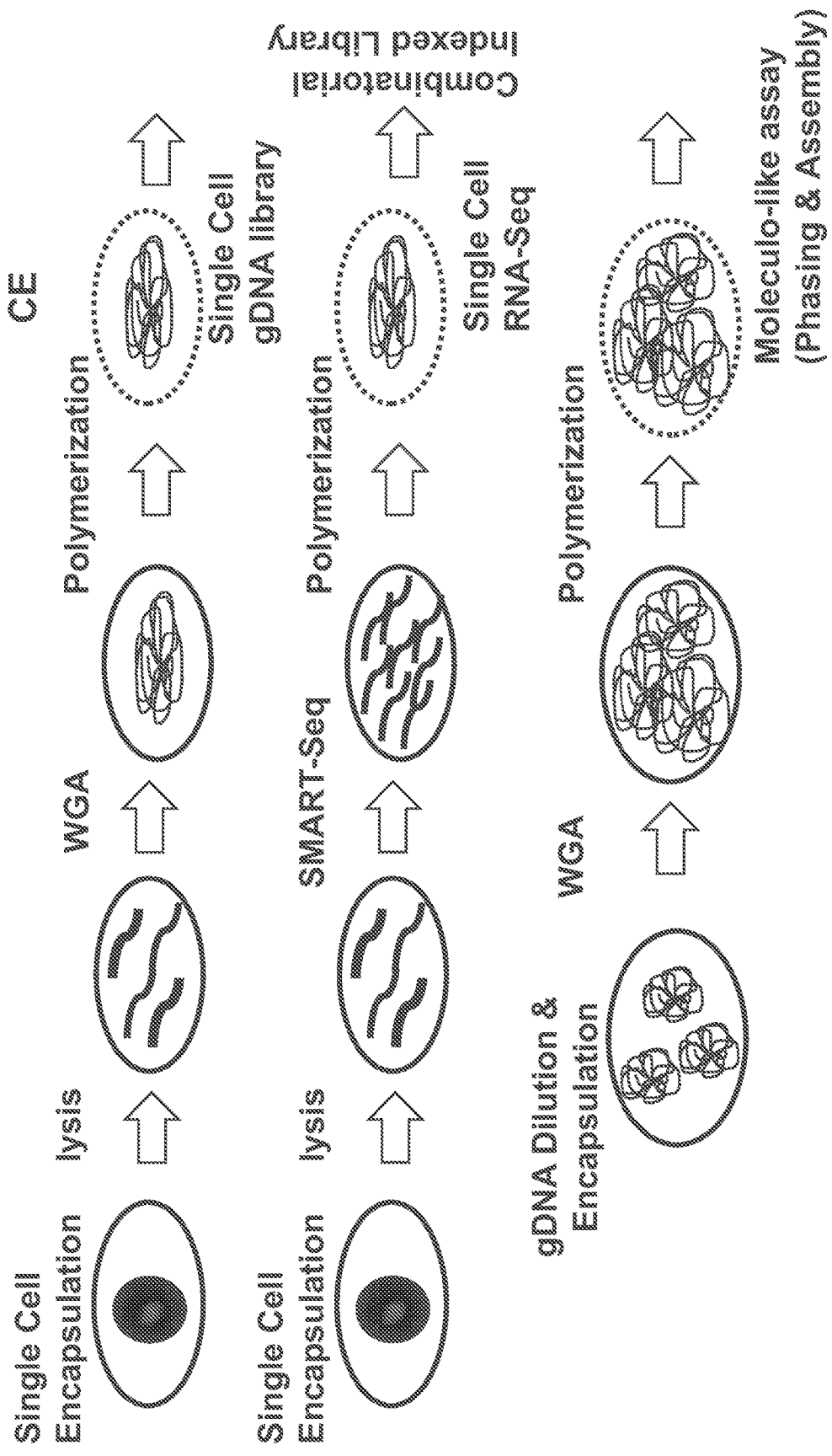

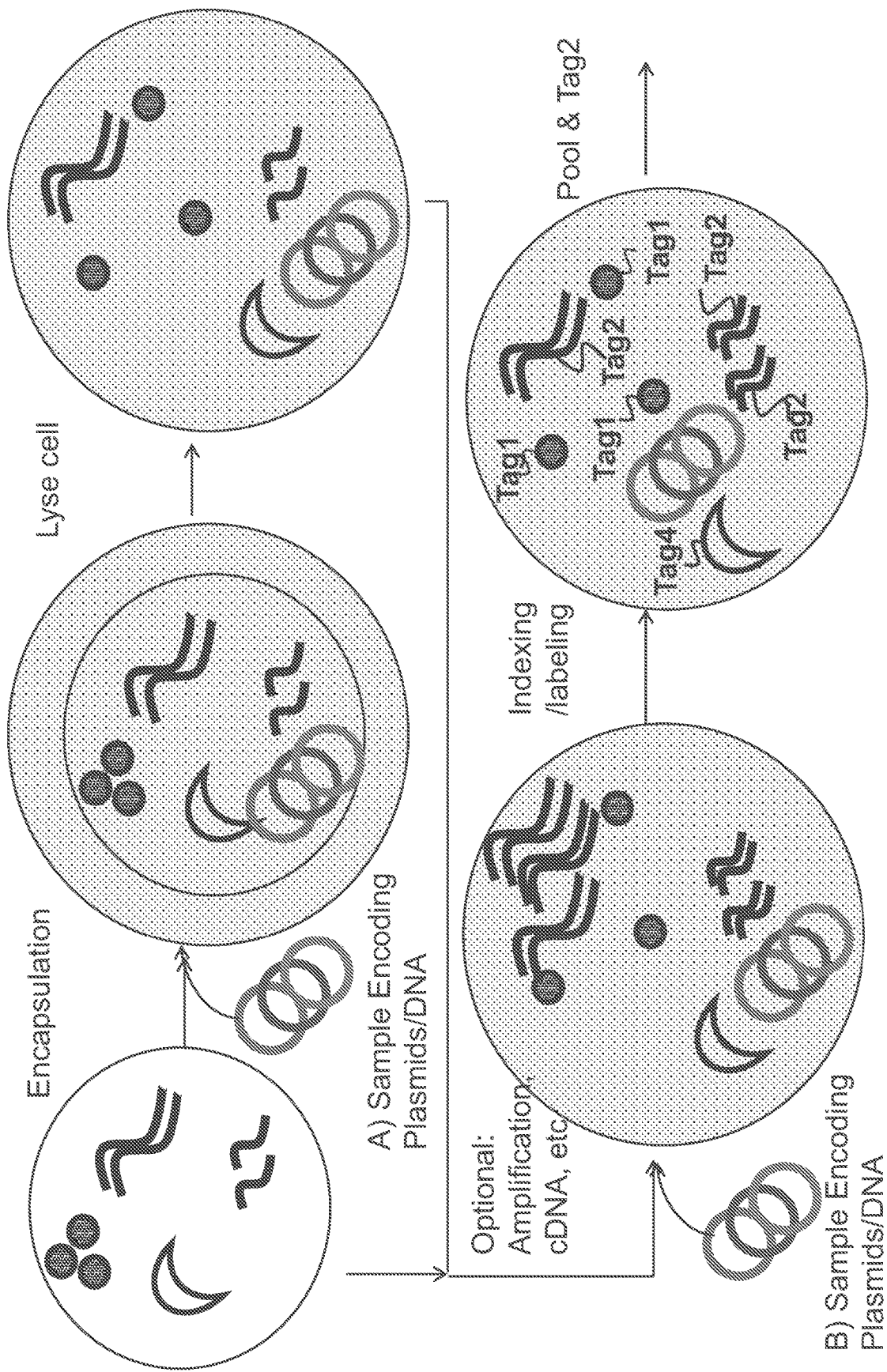

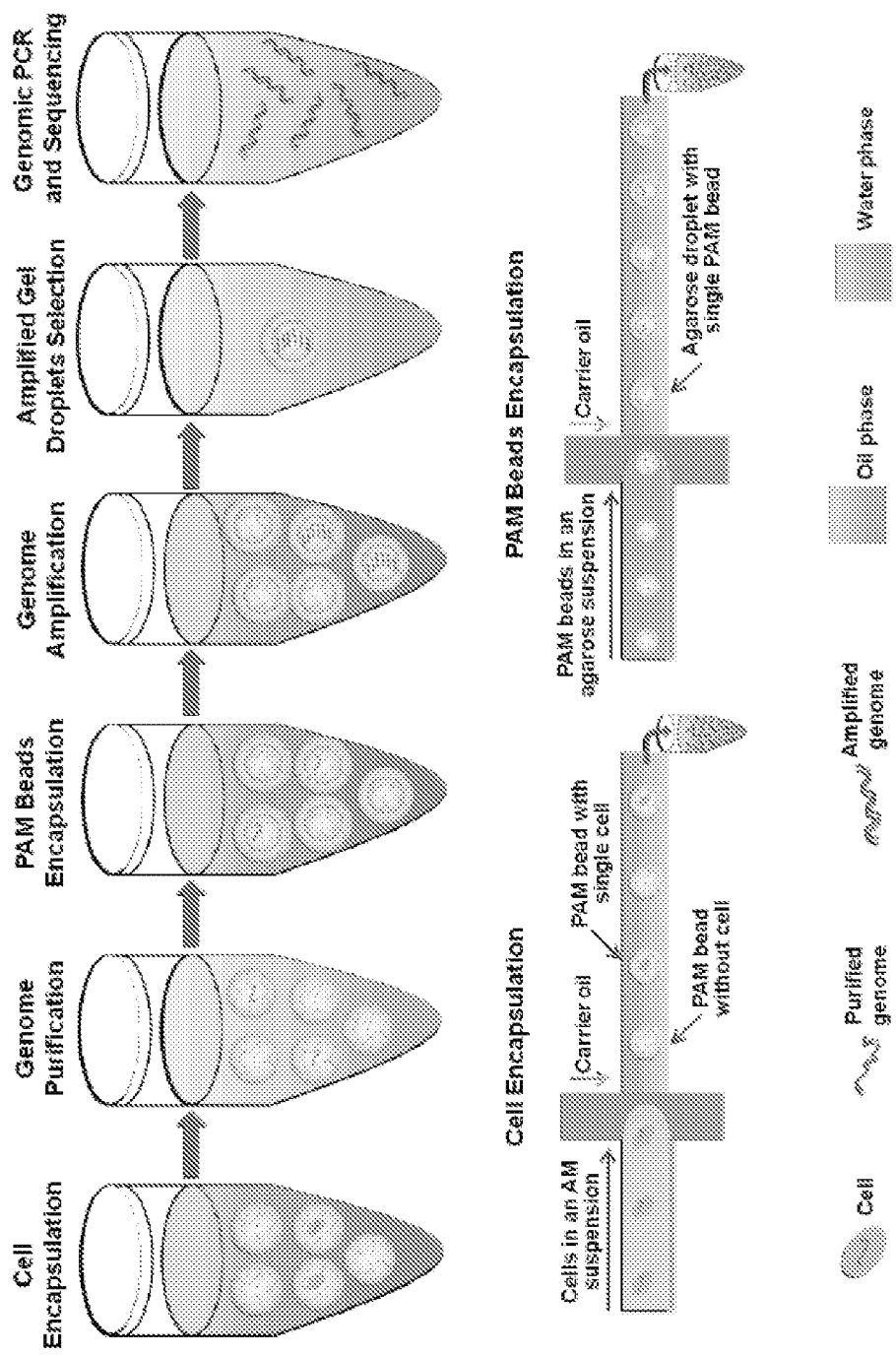
Fig. 6. Single Cell Encapsulation and Amplification
Scheme 1. Workflow diagram of strategy for high-throughput single-cell genomic sequencing

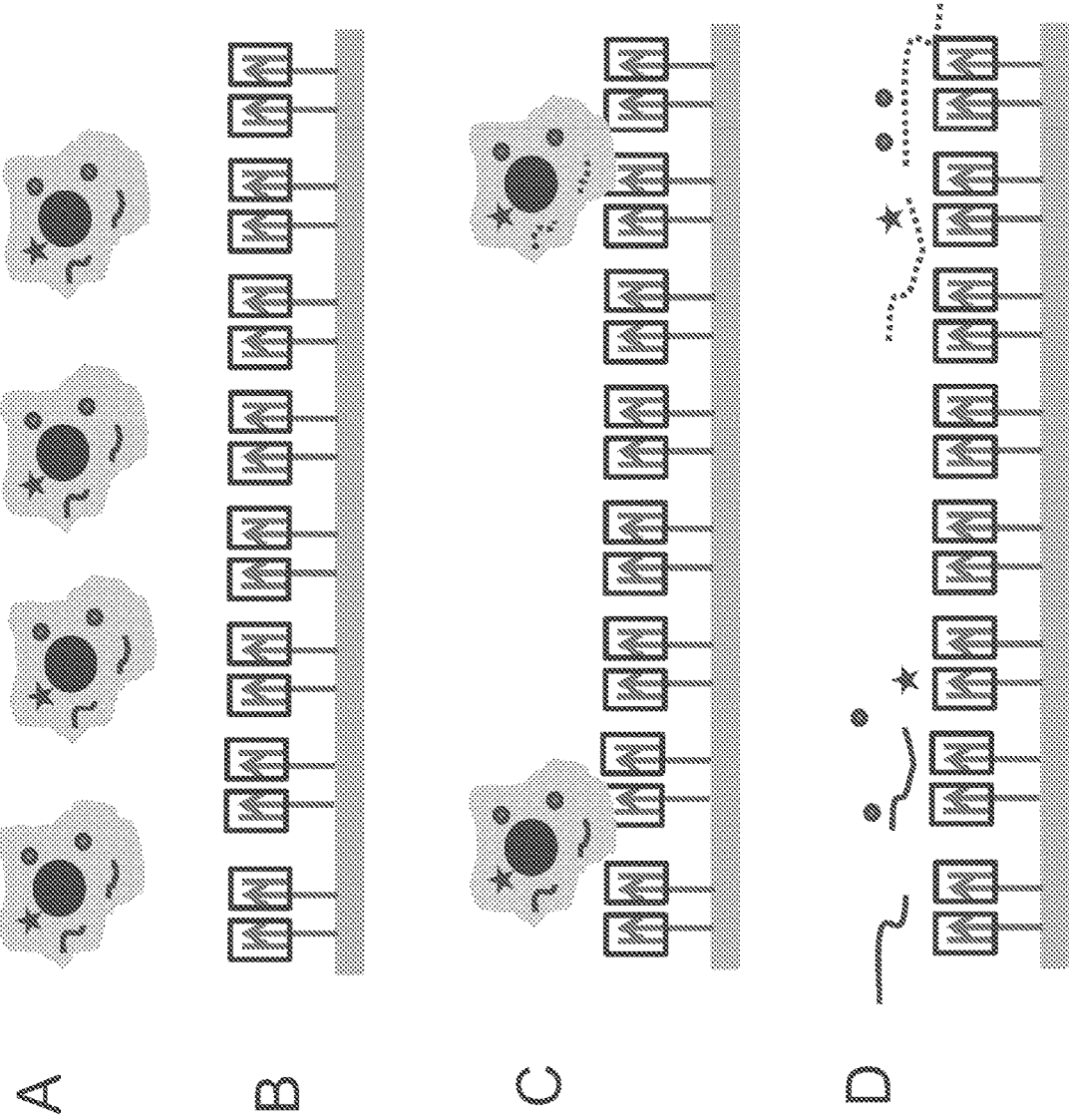
Fig. 7. High throughput analysis of cellular components by direct surface capture.

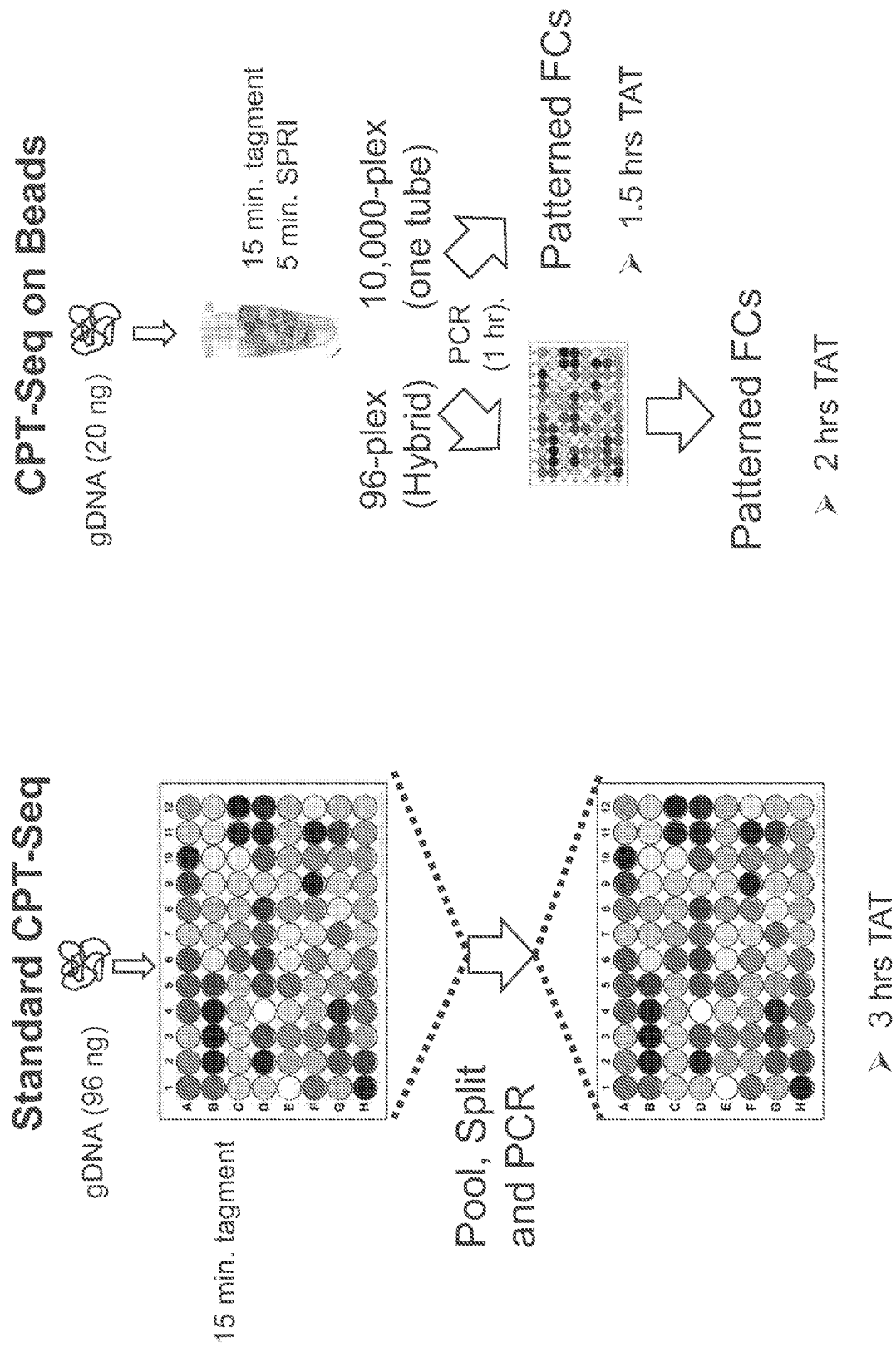
Fig. 8. Streamlining CPT-Seq: on bead workflow

Fig. 9A. Partitioning and Mutagenesis Approach to Assemble Repeat Regions in Genomic DNA comparison of 96 partitions to 46000 partitions Fig. 9B. Partitioning and Mutagenesis Approach to Assemble Repeat Regions in Genomic DNA

Experimental set up

- 10kb fragment
- 10 mutations each
- Long coverage = 10
- 20% C->T mutation
- Insert size = 500bp
- 2x300bp, no sequencing error
- Ecoli genome -> 46000 10kb fragments
- Spade assembler Fig. 9C. Partitioning and Mutagenesis Approach to Assemble Repeat Regions in Genomic DNA
96 partitions
- Distribution of the size of contigs reported by SPAde when analyzing in 96 partitions
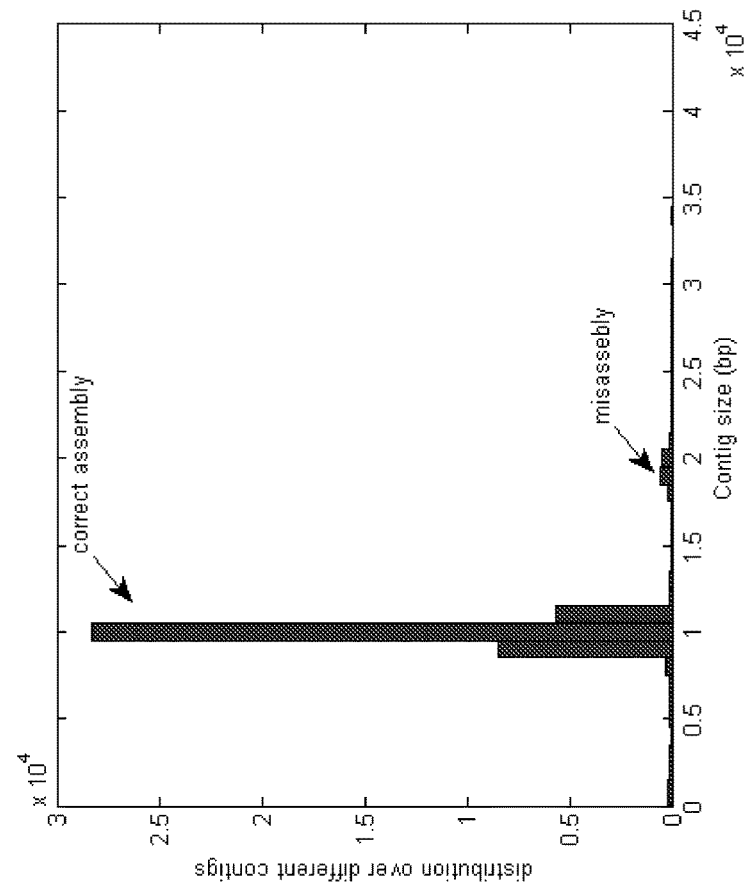

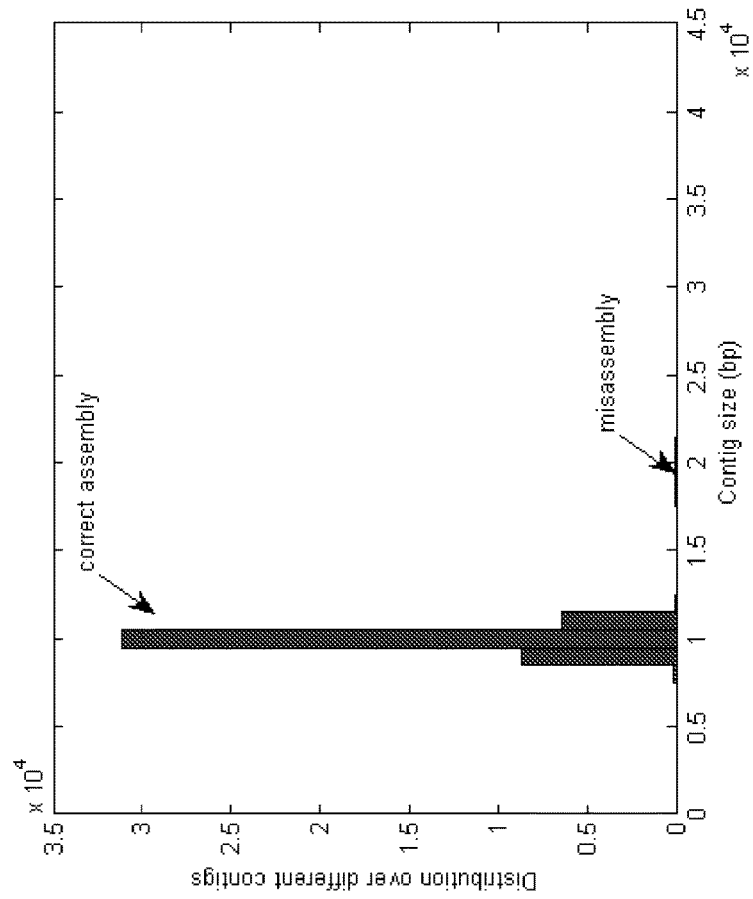
Fig. 9D. Partitioning and Mutagenesis Approach to Assemble Repeat Regions in Genomic DNA
46000 partitions
Distribution of the size of contigs reported by SPAde when analyzing in 46000 partitions (each 10kb fragment in a single partition)

METHODS AND COMPOSITIONS FOR ANALYZING CELLULAR COMPONENTS

RELATED APPLICATIONS

This application is a national stage entry of International Patent Application No. PCT/US2016/017391, filed Feb. 10, 2016, which further claims the benefits and priority of U.S. Provisional Patent Application No. 62/114,505 filed on Feb. 10, 2015. The entire disclosures of the above applications are incorporated by reference in their entirety.

SEQUENCE LISTING

The instant application contains a Sequence Listing which has been submitted electronically in ASCII format and is hereby incorporated by reference in its entirety. Said ASCII copy, created on May 20, 2016, is named IP-1296-US-_SL.txt and is 2,000 bytes in size.

FIELD OF THE DISCLOSURE

Embodiments of the present application relate to methods and composition for analyzing cellular components. In some embodiments, the present application relate to methods and composition for analyzing components of a single cell. In some embodiments, the present application relate to methods and composition for identifying a single cell type. In some embodiments, the methods and compositions relate to sequencing nucleic acids. Some embodiments of the methods and compositions provided are useful in deriving a composite status of such single cell.

BACKGROUND

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Nucleic acid sequencing methodology has evolved significantly from the chemical degradation methods used by Maxam and Gilbert and the strand elongation methods used by Sanger. Today several sequencing methodologies are in use which allow for the parallel processing of nucleic acids all in a single sequencing run. As such, the information generated from a single sequencing run can be enormous.

BRIEF DESCRIPTION OF THE DRAWINGS

FIG. 1 depicts a schematic of a four tier combinatoric indexing of DNA contiguity preserving element (CE) created by embedding single cell contents in a polymer matrix or attaching to a bead. Compartment-specific indexes are attached at each combinatoric pooling and redistribution step (tiers). In the example shown, the four tiers result in four indexes being concatenated together (via repeated rounds of ligation, polymerase extension, tagmentation, etc.) enabling easy sequencing read out. Alternatively, the contiguity preserving element comprising DNA can be created by a compartmentalized DNA partition (i.e. a DNA dilution subsampling the original DNA sample) that has been encapsulated in a matrix or immobilized on a bead. This type of dilution is useful in phasing and assembly applications.

FIG. 2 depicts a method of preparing single cell DNA or cDNA libraries using a two tier combinatorial indexing scheme wherein the first level indexes are attached via tagmentation (compartment-specific indexes in transposons) and the second tier indexes are attached by PCR (compartment-specific indexes on PCR primers). The contents of the single cell vessel (i.e. genomic DNA or cDNA) may employ an optional whole genome amplification (WGA) or whole transcriptome amplification step.

FIG. 3 depicts a method of making cDNA library from the contents of a single cell in CE such as droplets. In the example shown, the indexes are being used to label different samples.

FIG. 4 depicts representative contents of a single cell that can be analyzed via the combinatorial indexing scheme proposed.

FIGS. 5A and 5B depict exemplary schematic embodiments for creating a contiguity preserving elements (CE) from encapsulating and lysing the contents of a single cell trapped within a CE such as in polymer bead. Cell is embedded in, for example, a polymer bead. All the components from a single cell are kept in proximity to one another in the bead. Subsequently, one or more components can be amplified, modified (cDNA synthesis), and subsequently labeled with indexes or tags. FIG. 5C depicts an exemplary schematic embodiment in which sample indexing can be accomplished by spiking encoding DNA sequences (such as a plasmid) at the encapsulation, amplification/cDNA, or polymerization stage. Each sample is prepared with a different set of encoding plasmids or combination of encoding plasmid. Every combinatorially indexed CE will produce corresponding combinatorially indexed sample encoding library elements. In this way, every library element can be mapped back to its originating CE and originating sample.

FIG. 6 depicts schematics for encapsulating single cell contents in CE such as polymer matrix beads.

FIG. 8 depicts an exemplary schematics of analyzing nucleic acid using contiguity preserving elements on beads.

FIG. 9A-D depicts an exemplary modelling strategy.

DETAILED DESCRIPTION

Figure 7:
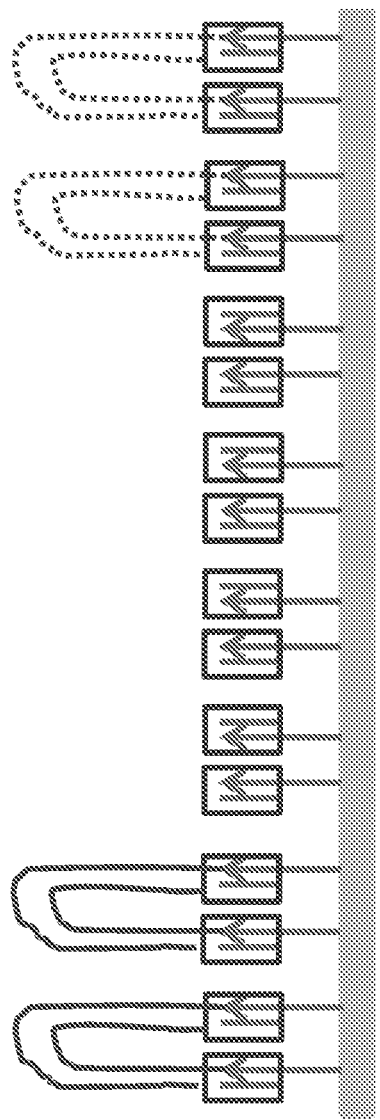
FIG. 7 depicts an exemplary schematics of high throughput analysis of cellular components by direct surface capture. "A" shows a collection of cells. "B" shows surface-bound transposomes. In "C" the cells are flowed onto the surface. In "D" cells are lysed and the cell's components are allowed to diffuse in a controlled way around the site at which the cell was captured. In "E" the nucleic acids are captured (tagmented) by the transposomes. Different cellular components are captured depending on whether the cell membrane or nuclei are lysed. By using component-specific capture moieties (i.e. antibodies, receptors, ligands), various cellular components can be captured. The analysis of the captured molecules can be carried out directly on the capturing surface. Alternatively, the captured molecules can be harvested and analysed on a different surface. In this case, the first surface is made up of multiple areas (i.e. pads) and each pad is coated with oligos that share an identical barcode so that molecules that are captured on the same pad will share the same identifying barcode.

Some aspects of the present invention relates to methods and compositions relating to evaluating components of a single cell preserved or embedded or contained within a contiguity preserving elements (CE).

In one aspect disclosed herein are methods for analyzing plurality of analyte types from a single cell. In some embodiments, a plurality of contiguity preserving elements (CE) are provided, each CE comprises a single cell. The cells are lysed within the CE such that the plurality of analytes within the single cell are released within the CE. In some embodiments, plurality of types of reporter moieties are provided such that each type of reporter moiety is specific for each type of analyte. In some embodiments, the reporter moiety identify a single cell. The plurality of analytes are modified such that each type of analyte comprise a reporter moiety specific for the analyte type. In some embodiments, the CE comprising the analytes comprising said reporter moieties are combined. In some embodiments, the combined CE comprising the analytes comprising said reporter moieties are compartmentalized. In some embodiments additional reporter moieties are provided and combined with the analytes comprising analytes such that the analytes comprise two or more different reporter moieties. The analytes comprising the reporter moieties are analyzed such that the identity of the analyte is detected and the reporter moiety identifies the source of the analyte from a single cell.

In some embodiments, the exemplary plurality of analytes include but are not limited to DNA, RNA, cDNA, protein, lipids, carbohydrates, cellular organelles, (e.g., nucleus, golgi apparatus, ribosomes, mitochondria, endoplasmic reticulum, chloroplast, cell membrane, etc.), cellular metabolites, tissue sections, cells, single cell, contents from cells or from a single cell, nucleic acid isolated from cells or from a single cell, or nucleic acid isolated from cells or from a single cell and further modified, or cell free DNA (e.g., from placental fluid or plasma). In some embodiments, the plurality of analytes include genomic DNA and mRNA. In some embodiments, the mRNA have poly A tail. In some embodiments, the genomic DNA and the mRNA are immobilized on a solid support within the CE simultaneously. In some embodiments, the immobilization of the genomic DNA is sequential to the immobilization of the mRNA to the solid support. In some embodiments, the genomic DNA is combined with transposome complexes and the transposon ends are immobilized on a solid support and the mRNA are immobilized to the solid by hybridization of oligo (dT) probes immobilized on a solid support. In some embodiments, the genomic DNA is combined with transposome complexes and, optionally, the transposon ends hybridize to complementary sequences immobilized on a solid support such that the mRNA are immobilized to the solid by hybridization of oligo (dT) probes immobilized on a solid support. Other methods can be used to immobilize the mRNA as well. In some embodiments, the solid support is a bead. In some embodiments, the solid support is a flow cell surface. In some embodiments, the solid surface is the wall of a reaction vessel.

In some embodiments, the methods include sequencing nucleic acids preserved or embedded or contained within CE. In particular, embodiments of the methods and compositions provided herein relate to preparing nucleic acid templates and obtaining sequence data therefrom. Methods and compositions provided herein are related to the methods and compositions provided in U.S. Patent Application Pub. No. 2012/0208705, U.S. Patent Application Pub. No. 2012/0208724 and Int. Patent Application Pub. No. WO 2012/061832, each of which is incorporated by reference in its entirety. Some embodiments of the present invention relate to preparing DNA within CE to obtain phasing and sequence assembly information from a target nucleic acid, and obtaining phasing and sequence assembly sequence information from such templates. Particular embodiments provided herein relate to the use of integrases, for example transposases, to maintain physical proximity of associated ends of fragmented nucleic acids; and to the use of combinatoric indexing to create individual libraries from each CE. Obtaining haplotype information from CE includes distinguishing between different alleles (e.g., SNPs, genetic anomalies, etc.) in a target nucleic acid. Such methods are useful to characterize different alleles in a target nucleic acid, and to reduce the error rate in sequence information.

In one embodiment, a template nucleic acid can be diluted into CE such as droplets. Optional whole genome amplification may be employed, and sequence information can be obtained from an amount of template nucleic acid equivalent to about a haploid equivalent of the target nucleic acid.

In further embodiments, a template nucleic acid can be compartmentalized such that multiple copies of a chromosome can be present in the same compartment, as a result of dual or multiple indexing provided herein, a haplotype can still also be determined. In other words, a template nucleic acid can be prepared using virtual compartments. In such embodiments, a nucleic acid can be distributed between several first compartments, providing a first index to the nucleic acid of each compartment, combining the nucleic acids, distributing the nucleic acid between several second compartments, and providing a second index to the nucleic acid of each compartment. Advantageously, such indexing enables haplotype information to be obtained at higher concentrations of nucleic acid compared to the mere dilution of a nucleic acid in a single compartment to an amount equivalent to a haplotype of the nucleic acid.

As used herein, the term "compartment" is intended to mean an area or volume that separates or isolates something from other things. Exemplary compartments include, but are not limited to, vials, tubes, wells, droplets, boluses, beads, vessels, surface features, or areas or volumes separated by physical forces such as fluid flow, magnetism, electrical current or the like.

Figure 10:
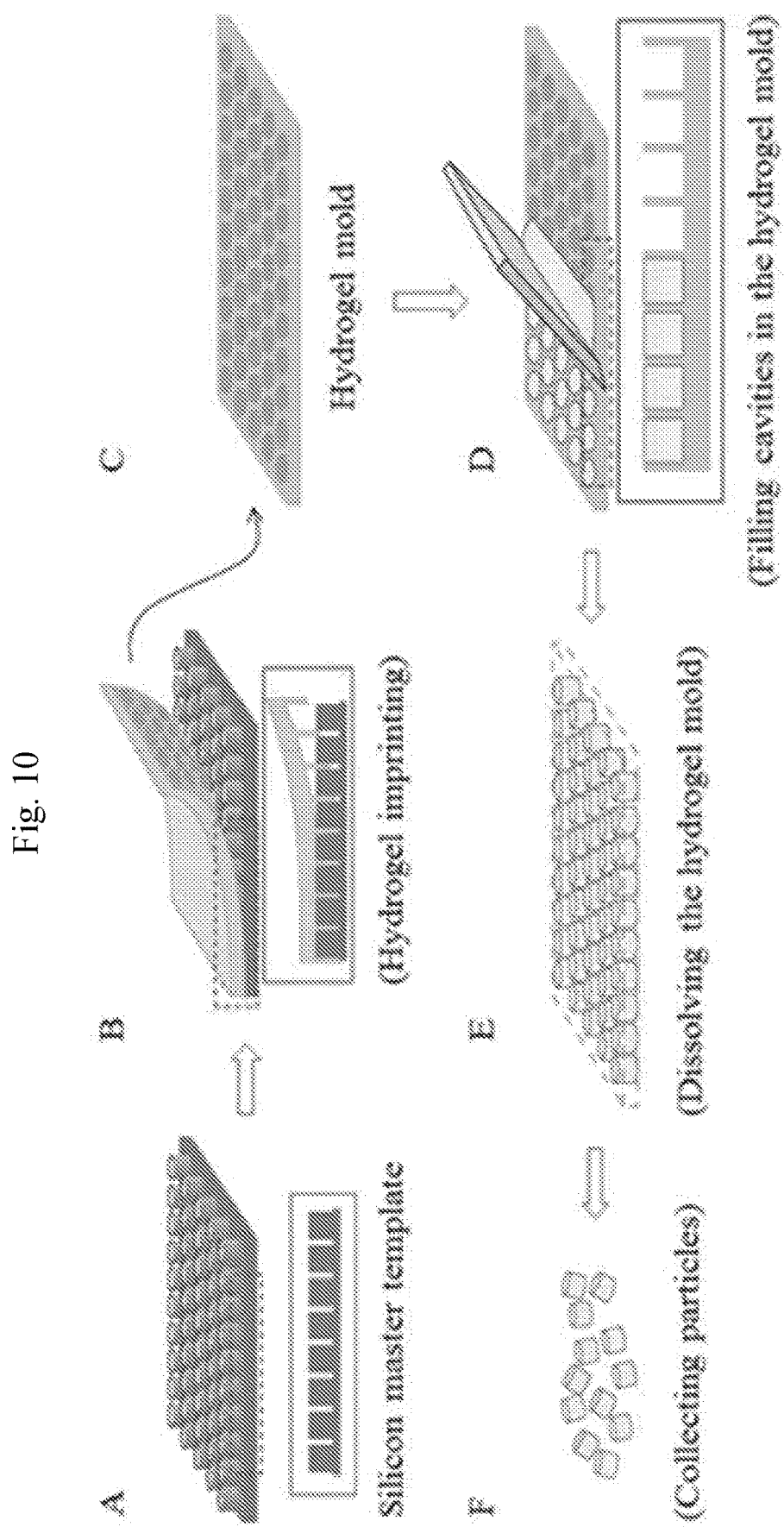
FIG. 10 shows a method for creating particles that are useful for creating contiguity elements.

An exemplary method for making compartments is shown in FIG. 10. A silicon master plate having posts can be used to imprint wells into a sheet of hydrogel (wells in the hydrogel are the reverse images of the posts). The resulting wells in the hydrogel can be filled with a material that forms particles (e.g. a gel or polymer) along with a target analyte or other reagent. The hydrogel sheet can then be dissolved by a technique that does not dissolve the particles. Then the particles can be collected and manipulated using methods set forth herein.

In some embodiments provided herein, template libraries are prepared using transposomes. In some such libraries, the target nucleic acid may be fragmented. Accordingly, some embodiments provided herein relate to methods for maintaining sequence information for the physical contiguity of adjacent fragments. Such methods include the use of integrases to maintain the association of template nucleic acid fragments adjacent in the target nucleic acid. Advantageously, such use of integrases to maintain physical proximity of fragmented nucleic acids increases the likelihood that fragmented nucleic acids from the same original molecule, e.g., chromosome, will occur in the same compartment.

Other embodiments provided herein relate to obtaining sequence information from each strand of a nucleic acid which can be useful to reduce the error rate in sequencing information. Methods to prepare libraries of template nucleic acids for obtaining sequence information from each strand of a nucleic acid can be prepared such that each strand can be distinguished, and the products of each strand can also be distinguished.

Some of the methods provided herein include methods of analyzing nucleic acids. Such methods include preparing a library of template nucleic acids of a target nucleic acid, obtaining sequence data from the library of template nucleic acids, and assembling a sequence representation of the target nucleic acid from such sequence data.

Generally, the methods and compositions provided herein are related to the methods and compositions provided in U.S. Patent Application Pub. No. 2012/0208705, U.S. Patent Application Pub. No. 2012/0208724 and Int. Patent Application Pub. No. WO 2012/061832, each of which is incorporated by reference in its entirety. The methods provided herein relate to the use of transposomes useful to insert features into a target nucleic acid. Such features include fragmentation sites, primer sites, barcodes, affinity tags, reporter moieties, etc.

In a method useful with the embodiments provided herein, a library of template nucleic acids is prepared from a CE comprising target nucleic acid. The library is prepared by inserting or affixing a plurality of unique barcodes throughout the target nucleic acid. In some embodiments, each barcode includes a first barcode sequence and a second barcode sequence, having a fragmentation site disposed therebetween. The first barcode sequence and second barcode sequence can be identified or designated to be paired with one another. The pairing can be informative so that a first barcode is associated with a second barcode. Advantageously, the paired barcode sequences can be used to assemble sequencing data from the library of template nucleic acids. For example, identifying a first template nucleic acid comprising a first barcode sequence and a second template nucleic acid comprising a second barcode sequence that is paired with the first indicates that the first and second template nucleic acids represent sequences adjacent to one another in a sequence representation of the target nucleic acid. Such methods can be used to assemble a sequence representation of a target nucleic acid de novo, without the requirement of a reference genome.

In some embodiments, multiple combinatorial barcoding may be employed such that target nucleic acid from each single cell comprises a unique barcode (e.g. unique combination of barcodes) and can be easily identified from a different target nucleic acid from a different single cell. In some embodiments a CE may comprise the target nucleic acid from a single cell. In some embodiments, the target nucleic acid within a CE will have identifiable unique barcodes that are different from target nucleic acid within a different CE.

In some embodiments, multiple combinatorial labeling scheme may be employed to the components within a single cell in addition to the nucleic acid, for example, proteins, organelles, lipids, or cell membranes such that the components within a single cell can be identified from the components from a different single cell. In some embodiments, a CE may comprise the components within a single cell. In some embodiments, the components of a single cell within a CE will have identifiable unique label(s) that are different from the components of a single cell within a different CE.

In some embodiments, multiple combinatorial barcoding schemes may be employed to the target nucleic acid from a single cell and multiple combinatorial labeling schemes may be employed to the components within a single cell together.

In some embodiments, such combinatorial barcoding and combinatorial labeling may be performed within a CE comprising a single cell. In some embodiments, such combinatorial barcoding and combinatorial labeling may be performed for multiple CE comprising single cells in parallel.

In some embodiments, the proteins preserved, embedded, immobilized, or contained within CE may be sequenced. In some embodiments, such proteins are uniquely labeled. In some embodiments, the proteins preserved, embedded, immobilized, or contained within CE may be identified by methods known in the art. In some embodiments, the identification and or sequencing of the protein can be carried out together with gathering sequence information of the nucleic acids.

As used herein the term "nucleic acid" and/or "oligonucleotide" and/or grammatical equivalents thereof can refer to at least two nucleotide monomers linked together. A nucleic acid can generally contain phosphodiester bonds; however, in some embodiments, nucleic acid analogs may have other types of backbones, comprising, for example, phosphoramide (Beaucage, et al., *Tetrahedron*, 49:1925 (1993); Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., J. Am. Chem. Soc., 111:2321 (1989), O-methylphosphoroamidite linkages (see Eckstein, *Oligonucleotides and Analogues: A Practical Approach*, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996)). The above references are incorporated herein by reference.

Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., *J. Am. Chem. Soc.*, 110:4470 (1988); Letsinger, et al., *Nucleosides & Nucleotides*, 13:1597 (1994); Chapters 2 and 3, *ASC Symposium* Series 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose (U.S. Pat. Nos. 5,235,033 and 5,034,506, and Chapters 6 and 7, *ASC Symposium* Series 580, "Carbohydrate Modifications in Antisense Research", Ed. Y. S. Sanghui and P. Dan Coo). Nucleic acids may also contain one or more carbocyclic sugars (see Jenkins, et al., Chem. Soc. Rev., (1995) pp. 169 176). The above references are incorporated herein by reference.

Modifications of the ribose-phosphate backbone may be done to facilitate the addition of additional moieties such as labels, or to increase the stability of such molecules under certain conditions. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, for example, genomic or cDNA, RNA or a hybrid, from single cells, multiple cells, or from multiple species, as with metagenomic samples, such as from environmental samples, further from mixed samples for example mixed tissue samples or mixed samples for different individuals of the same species, disease samples such as cancer related nucleic acids, and the like. A nucleic acid can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc.

In some embodiments, a nucleic acid can include at least one promiscuous base. Promiscuous bases can base-pair with more than one different type of base. In some embodiments, a promiscuous base can base-pair with at least two different types of bases and no more than three different types of bases. An example of a promiscuous base includes inosine that may pair with adenine, thymine, or cytosine. Other examples include hypoxanthine, 5-nitroindole, acrylic 5-nitroindole, 4-nitropyrazole, 4-nitroimidazole and 3-nitropyrrole (Loakes et al., *Nucleic Acid Res.* 22:4039 (1994); Van Aerschot et al., *Nucleic Acid Res.* 23:4363 (1995); Nichols et al., *Nature* 369:492 (1994); Bergstrom et al., *Nucleic Acid Res.* 25:1935 (1997); Loakes et al., *Nucleic Acid Res.* 23:2361 (1995); Loakes et al., *J. Mol. Biol.* 270:426 (1997); and Fotin et al., *Nucleic Acid Res.* 26:1515 (1998)). Promiscuous bases that can base-pair with at least three, four or more types of bases can also be used. The above references are incorporated herein by reference.

As used herein, the term "nucleotide analog" and/or grammatical equivalents thereof can refer to synthetic analogs having modified nucleotide base portions, modified pentose portions, and/or modified phosphate portions, and, in the case of polynucleotides, modified internucleotide linkages, as generally described elsewhere (e.g., Scheit, Nucleotide Analogs, John Wiley, New York, 1980; Englisch, Angew. *Chem. Int. Ed. Engl.* 30:613-29, 1991; Agarwal, *Protocols for Polynucleotides and Analogs*, Humana Press, 1994; and S. Verma and F. Eckstein, *Ann. Rev. Biochem.* 67:99-134, 1998). Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counter ions, e.g., $H^+$, $NH_4^+$, $Na^+$, if such counter ions are present. Example modified nucleotide base portions include but are not limited to 5-methylcytosine (5mC); C-5-propynyl analogs, including but not limited to, C-5 propynyl-C and C-5 propynyl-U; 2, 6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, 5-Me-Bz-C-LNA, dmf-G-LNA, and T-LNA (see, e.g., *The Glen Report,* 16(2): 5, 2003; Koshkin et al., *Tetrahedron* 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged inter-subunit linkages (e.g., Sterchak, E. P. et al., Organic Chem., 52:4202, 1987), and uncharged morpholino-based polymers having achiral inter-subunit linkages (see, e.g., U.S. Pat. No. 5,034,506). Some internucleotide linkage analogs include morpholidate, acetal, and polyamide-linked heterocycles. In one class of nucleotide analogs, known as peptide nucleic acids, including pseudo complementary peptide nucleic acids ("PNA"), a conventional sugar and internucleotide linkage has been replaced with a 2-aminoethylglycine amide backbone polymer (see, e.g., Nielsen et al., *Science,* 254:1497-1500, 1991; Egholm et al., *J. Am. Chem. Soc.,* 114: 1895-1897 1992; Demidov et al., *Proc. Natl. Acad. Sci.* 99:5953-58, 2002; *Peptide Nucleic Acids: Protocols and Applications*, Nielsen, ed., Horizon Bioscience, 2004). The above references are incorporated herein by reference.

As used herein, the term "sequencing read" and/or grammatical equivalents thereof can refer to a repetitive process of physical or chemical steps that is carried out to obtain signals indicative of the order of monomers in a polymer. The signals can be indicative of an order of monomers at single monomer resolution or lower resolution. In particular embodiments, the steps can be initiated on a nucleic acid target and carried out to obtain signals indicative of the order of bases in the nucleic acid target. The process can be carried out to its typical completion, which is usually defined by the point at which signals from the process can no longer distinguish bases of the target with a reasonable level of certainty. If desired, completion can occur earlier, for example, once a desired amount of sequence information has been obtained. A sequencing read can be carried out on a single target nucleic acid molecule or simultaneously on a population of target nucleic acid molecules having the same sequence, or simultaneously on a population of target nucleic acids having different sequences. In some embodiments, a sequencing read is terminated when signals are no longer obtained from one or more target nucleic acid molecules from which signal acquisition was initiated. For example, a sequencing read can be initiated for one or more target nucleic acid molecules that are present on a solid phase substrate and terminated upon removal of the one or more target nucleic acid molecules from the substrate. Sequencing can be terminated by otherwise ceasing detection of the target nucleic acids that were present on the substrate when the sequencing run was initiated.

As used herein, the term "sequencing representation" and/or grammatical equivalents thereof can refer to information that signifies the order and type of monomeric units in the polymer. For example, the information can indicate the order and type of nucleotides in a nucleic acid. The information can be in any of a variety of formats including, for example, a depiction, image, electronic medium, series of symbols, series of numbers, series of letters, series of colors, etc. The information can be at single monomer resolution or at lower resolution. An exemplary polymer is a nucleic acid, such as DNA or RNA, having nucleotide units. A series of "A," "T," "G," and "C" letters is a well-known sequence representation for DNA that can be correlated, at single nucleotide resolution, with the actual sequence of a DNA molecule. Other exemplary polymers are proteins having amino acid units and polysaccharides having saccharide units.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

As used herein, the term "detect" and/or grammatical equivalents thereof can refer to identifying the presence or existence of an analyte, identifying the individual components of an analyte, for example, sequence information, and/or quantifying the amount of such analyte.

Fragmentation Sites

In some embodiments comprising looped transposomes, the linker can comprise a fragmentation site. A fragmentation site can be used to cleave the physical, but not the informational association between a first barcode sequence and a second barcode sequence. Cleavage may be by biochemical, chemical or other means. In some embodiments, a fragmentation site can include a nucleotide or nucleotide sequence that may be fragmented by various means. For example, a fragmentation site may comprise a restriction endonuclease site; at least one ribonucleotide cleavable with an RNAse; nucleotide analogues cleavable in the presence of certain chemical agent; a diol linkage cleavable by treatment with periodate; a disulfide group cleavable with a chemical reducing agent; a cleavable moiety that may be subject to photochemical cleavage; and a peptide cleavable by a peptidase enzyme or other suitable means. See e.g., U.S. Patent Application Pub. No. 2012/0208705, U.S. Patent Application Pub. No. 2012/0208724 and Int. Patent Application Pub. No. WO 2012/061832, each of which is incorporated by reference in its entirety.

Primer Sites

In some embodiments, the reporter moieties may comprise primer sites that can hybridize to a primer. In some embodiments, a reporter moiety can include at least a first primer site useful for amplification, sequencing, and the like.

In some embodiments, a transposon sequence can include a "sequencing adaptor" or "sequencing adaptor site", that is to say a region that comprises one or more sites that can hybridize to a primer. In some embodiments, a transposon sequence can include at least a first primer site useful for amplification, sequencing, and the like. In some embodiments comprising looped transposomes, a linker can include a sequencing adaptor. In more embodiments comprising looped transposomes, a linker comprises at least a first primer site and a second primer site. The orientation of the primer sites in such embodiments can be such that a primer hybridizing to the first primer site and a primer hybridizing to the second primer site are in the same orientation, or in different orientations.

In some embodiments, a linker can include a first primer site, a second primer site having a non-amplifiable site disposed therebetween. The non-amplifiable site is useful to block extension of a polynucleotide strand between the first and second primer sites, wherein the polynucleotide strand hybridizes to one of the primer sites. The non-amplifiable site can also be useful to prevent concatamers. Examples of non-amplifiable sites include a nucleotide analogue, non-nucleotide chemical moiety, amino-acid, peptide, and polypeptide. In some embodiments, a non-amplifiable site comprises a nucleotide analogue that does not significantly base-pair with A, C, G or T. Some embodiments include a linker comprising a first primer site, a second primer site having a fragmentation site disposed therebetween. Other embodiments can use a forked or Y-shaped adapter design useful for directional sequencing, as described in U.S. Pat. No. 7,741,463, the disclosure of which is incorporated herein by reference in its entirety.

Exemplary sequences of primer binding sites include, but are not limited to AATGATACGGCGACCACCGAGATC-TACAC (P5 sequence) and CAAGCAGAAGACGGCAT-ACGAGAT (P7 sequence).

Reporter Moieties

As used herein, the term "reporter moiety" and grammatical equivalents can refer to any identifiable tag, label, indices, barcodes, or group that enables to determine the composition, identity, and/or the source of an analyte that is investigated.

The skilled artisan will appreciate that many different species of reporter moieties can be used with the methods and compositions described herein, either individually or in combination with one or more different reporter moieties. In some embodiments, more that one different reporter moieties may be used to simultaneously analyze more than one analyte. In some embodiments, a plurality of different reporter moieties may be used simultaneously to uniquely identify single cell or components of a single cell.

In certain embodiments, a reporter moiety can emit a signal. Examples of a signal includes, but is not limited to, a fluorescent, a chemiluminescent, a bioluminescent, a phosphorescent, a radioactive, a calorimetric, an ion activity, an electronic or an electrochemiluminescent signals. Example reporter moieties are listed, for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

In some embodiments, reporter moiety may be an adapter. In some embodiments of the compositions and methods described herein, a transposon sequence can include a reporter moiety. In some embodiments comprising looped transposomes, a linker or adapter can comprise a reporter moiety.

In some embodiments, a reporter moiety may not emit a signal. In some embodiments, a reporter moiety may be a nucleic acid fragment such as a barcode, unique molecular index, a plasmid. In some embodiments, a reporter moiety may comprise an antibody that specifically binds to a protein. In some embodiments, the antibody may comprise a detectable label. In some embodiments, the reporter can include an antibody or affinity reagent labeled with a nucleic acid tag. The nucleic acid tag can be detectable, for example, via a proximity ligation assay (PLA) or proximity extension assay (PEA).

In some embodiments, a set of reporter moieties may be used. In some embodiments, the set of reporter moieties may comprise a mixture of subset of reporter moieties, in which each subset of the reporter moieties are specific for a different type of analyte, for example, proteins, nucleic acids, lipids, carbohydrates. In some embodiments, the set of reporter moieties may comprise a mixture of subset of reporter moieties, in which each subset of the reporter moieties are different from each other, but are specific for a same type of analyte.

Barcodes

Generally, a barcode can include one or more nucleotide sequences that can be used to identify one or more particular analytes, such as nucleic acids, proteins, metabolites or other analytes set forth herein or known in the art. The barcode can be an artificial sequence, or can be a naturally occurring sequence generated during transposition, such as identical flanking genomic DNA sequences (g-codes) at the end of formerly juxtaposed DNA fragments. A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated.

In some embodiments, a transposon sequence comprises at least one barcode. In some embodiments, such as transposomes comprising two non-contiguous transposon sequences, the first transposon sequence comprises a first barcode, and the second transposon sequence comprises a second barcode. In some embodiments, such as in looped transposomes, a transposon sequence comprises a barcode comprising a first barcode sequence and a second barcode sequence. In some of the foregoing embodiments, the first barcode sequence can be identified or designated to be paired with the second barcode sequence. For example, a known first barcode sequence can be known to be paired with a known second barcode sequence using a reference table comprising a plurality of first and second bar code sequences known to be paired to one another.

In another example, the first barcode sequence can comprise the same sequence as the second barcode sequence. In another example, the first barcode sequence can comprise the reverse complement of the second barcode sequence. In some embodiments, the first barcode sequence and the second barcode sequence are different. The first and second barcode sequences may comprise a bi-code.

In some embodiments of compositions and methods described herein, barcodes are used in the preparation of template nucleic acids. As will be understood, the vast number of available barcodes permits each template nucleic acid molecule to comprise a unique identification. Unique identification of each molecule in a mixture of template nucleic acids can be used in several applications. For example, uniquely identified molecules can be applied to identify individual nucleic acid molecules, in samples having multiple chromosomes, in genomes, in cells, in cell types, in cell disease states, and in species, for example, in haplotype sequencing, in parental allele discrimination, in metagenomic sequencing, and in sample sequencing of a genome. Exemplary barcode sequences include, but are not limited to TATAGCCT, ATAGAGGC, CCTATCCT, GGCTCTGA, AGGCGAAG, TAATCTTA, CAGGACGT, and GTACTGAC.

Linkers

Some embodiments comprising looped transposomes include transposon sequences comprising a first barcode sequence and a second barcode sequence having a linker disposed therebetween. In other embodiments, the linker can be absent, or can be the sugar-phosphate backbone that connects one nucleotide to another. The linker can comprise, for example, one or more of a nucleotide, a nucleic acid, a non-nucleotide chemical moiety, a nucleotide analogue, amino acid, peptide, polypeptide, or protein. In preferred embodiments, a linker comprises a nucleic acid. The linker can comprise at least about 1, 2, 3, 4, 5, 6, 7, 8, 9, 10, 11, 12, 13, 14, 15, 16, 17, 18, 19, 20, or more nucleotides. In some embodiments, a linker can comprise at least about 10, 20, 30, 40, 50, 60, 70, 80, 90, 100, 200, 300, 400, 500 or more nucleotides.

In some embodiments, a linker can be amplifiable for example by PCR, rolling circle amplification, strand displacement amplification, and the like. In other embodiments, a linker can comprise non-amplifiable moieties. Examples of non-amplifiable linkers include organic chemical linkers such as alkyl, propyl, PEG; non-natural bases such as IsoC, isoG; or any group that does not amplify in DNA-based amplification schemes. For example, transposons containing isoC, isoG pairs can be amplified with dNTPs mixtures lacking a complementary isoG and isoC, ensuring that no amplification occurs across the inserted transposons.

In some embodiments, the linker comprises a single-stranded nucleic acid. In some embodiments, the linker couples transposon sequences in a 5'-3' orientation, a 5'-5' orientation, or a 3'-3' orientation.

Affinity Tags

In some embodiments, a transposon sequence can include an affinity tag. In some embodiments comprising looped transposomes, a linker can comprise an affinity tag. Affinity tags can be useful for a variety of applications, for example the bulk separation of target nucleic acids hybridized to hybridization tags. Additional applications include, but are not limited to, using affinity tags for purifying transposase/transposon complexes and transposon inserted target DNA, target RNA or target proteins, for example. As used herein, the term "affinity tag" and grammatical equivalents can refer to a component of a multi-component complex, wherein the components of the multi-component complex specifically interact with or bind to each other. For example an affinity tag can include biotin or poly-His that can bind streptavidin or nickel, respectively. Other examples of multiple-component affinity tag complexes are listed, for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

Solid Support

A solid support can be two- or three-dimensional and can comprise a planar surface (e.g., a glass slide) or can be shaped. A solid support can include glass (e.g., controlled pore glass (CPG)), quartz, plastic (such as polystyrene (low cross-linked and high cross-linked polystyrene), polycarbonate, polypropylene and poly(methylmethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional solid supports include, for example, spheres, microparticles, beads, nanoparticles, polymer matrices such as agarose, polyacrylamide, alginate, membranes, slides, plates, micromachined chips, tubes (e.g., capillary tubes), microwells, microfluidic devices, channels, filters, flow cells, structures suitable for immobilizing a nucleic acid, proteins, or cells. A solid support can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

In some embodiments, the solid support comprises microspheres or beads. By "microspheres" or "beads" or "particles" or grammatical equivalents herein is meant small discrete particles. Suitable bead compositions include, but are not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and teflon, as well as any other materials outlined herein for solid supports may all be used. "Microsphere Detection Guide" from Bangs Laboratories, Fishers Ind. is a helpful guide. In certain embodiments, the microspheres are magnetic microspheres or beads. In some embodiments, the beads can be color coded. For example, MicroPlex® Microspheres from Luminex, Austin, Tex. may be used.

The beads need not be spherical; irregular particles may be used. Alternatively or additionally, the beads may be porous. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller or larger beads may be used. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 µm in diameter.

In some embodiments, the beads can comprise antibodies or other affinity probes (see Immobilized Biomolecules in Analysis. A Practical Approach. Cass T, Ligler F S, eds. Oxford University Press, New York, 1998. pp 1-14, incorporated herein by reference, for typical attachment protocols). In some embodiments, the antibodies can be monoclonal and in other embodiments, the antibodies can be polyclonal. In some embodiments, the antibodies can be specific for a cell surface epitope. In some embodiments, the antibodies can be specific for a protein inside the cell.

In some embodiments, the nucleic acid template provided herein can be attached to a solid support. Various methods well known in the art can be used to attach, anchor or immobilize nucleic acids to the surface of the solid support.

Analytes

Analytes are biomolecules whose function, composition, identity, and/or its source are investigated. Exemplary analytes include but are not limited to DNA, RNA, cDNA, protein, lipids, carbohydrates, cellular organelles, (e.g., nuclei, golgi apparatus, ribosomes, mitochondria, endoplasmic reticulum, chloroplast, cell membrane, etc.), cellular metabolites, tissue sections, cells, single cell, contents from cells or from a single cell, nucleic acid isolated from cells or from a single cell, or nucleic acid isolated from cells or from a single cell and further modified, or cell free DNA (e.g., from placental fluid or plasma).

Target Nucleic Acids

A target nucleic acid can include any nucleic acid of interest. In one embodiment, target nucleic acid can include any nucleic acid of interest contained, trapped, embedded, or immobilized within CE such as a matrix, droplet, emulsion, solid support, or compartment maintaining the contiguity of the nucleic acids within but allowing accessibility to liquids and enzymatic reagents. Target nucleic acids can include DNA, cDNA, products of WGA, RNA, peptide nucleic acid, morpholino nucleic acid, locked nucleic acid, glycol nucleic acid, threose nucleic acid, mixed samples of nucleic acids, polyploidy DNA (i.e., plant DNA), mixtures thereof, and hybrids thereof. In a preferred embodiment, genomic DNA fragments or amplified copies thereof are used as the target nucleic acid. In another preferred embodiment, cDNA, mitochondrial DNA or chloroplast DNA is used.

A target nucleic acid can comprise any nucleotide sequence. In some embodiments, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500 or 1000 nucleotides or more. Repeat sequences can be repeated, either contiguously or non-contiguously, any of a variety of times including, for example, 2, 3, 4, 5, 6, 7, 8, 9, 10, 15 or 20 times or more.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats so that reagents are delivered simultaneously to the target nucleic acids, for example, in one or more chambers or on an array surface. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Envinia, Agrobacterium, Rhizobium,* and *Streptomyces* genera); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (e.g., *Caenorhabditis elegans*), and mammals (for example, rat, mouse, monkey, non-human primate and human).

Target nucleic acids and template nucleic acids can be enriched for certain sequences of interest using various methods well known in the art. Examples of such methods are provided in Int. Pub. No. WO/2012/108864, which is incorporated herein by reference in its entirety. In some embodiments, nucleic acids may be further enriched during methods of preparing template libraries. For example, nucleic acids may be enriched for certain sequences, before insertion of transposomes, after insertion of transposomes, and/or after amplification of nucleic acids.

In addition, in some embodiments, target nucleic acids and/or template nucleic acids can be highly purified, for example, nucleic acids can be at least about 70%, 80%, 90%, 95%, 96%, 97%, 98%, 99%, or 100% free from contaminants before use with the methods provided herein. In some embodiments, it is beneficial to use methods known in the art that maintain the quality and size of the target nucleic acid, for example isolation and/or direct transposition of target DNA may be performed using agarose plugs.

In some embodiments, target nucleic acid may be obtained from a biological sample or a patient sample. The term "biological sample" or "patient sample" as used herein includes samples such as one or more cells, tissues or bodily fluids. "Bodily fluids" may include, but are not limited to, blood, serum, plasma, saliva, cerebral spinal fluid, pleural fluid, tears, lactal duct fluid, lymph, sputum, urine, amniotic fluid, or semen. A sample may include a bodily fluid that is "acellular." An "acellular bodily fluid" includes less than about 1% (w/w) whole cellular material. Plasma or serum are examples of acellular bodily fluids. A sample may include a specimen of natural or synthetic origin (i.e., a cellular sample made to be acellular).

The term "Plasma" as used herein refers to acellular fluid found in blood. "Plasma" may be obtained from blood by removing whole cellular material from blood by methods known in the art (e.g., centrifugation, filtration, and the like).

Certain Methods of Preparing Template Nucleic Acids

Some embodiments include methods of preparing template nucleic acids. As used herein, "template nucleic acid" can refer to a substrate for obtaining sequence information. In some embodiments, a template nucleic acid can include a target nucleic acid, a fragment thereof, or any copy thereof comprising at least one transposon sequence, a fragment thereof, or any copy thereof. In some embodiments, a template nucleic acid can include a target nucleic acid comprising a sequencing adaptor, such as a sequencing primer site. In some embodiments, the CE may comprise a target nucleic acid.

Some methods of preparing template nucleic acids include inserting a transposon sequence into a target nucleic acid, thereby preparing a template nucleic acid. Some methods of insertion include contacting a transposon sequence provided herein with a target nucleic acid in the presence of an enzyme, such as a transposase or integrase, under conditions sufficient for the integration of the transposon sequence or sequences into the target nucleic acid. In some embodiments, a CE may comprise such target nucleic acid.

In some embodiments, insertion of transposon sequences into a target nucleic acid can be non-random. In some embodiments, transposon sequences can be contacted with target nucleic acids comprising proteins that inhibit integration at certain sites. For example, transposon sequences can be inhibited from integrating into genomic DNA comprising proteins, genomic DNA comprising chromatin, genomic DNA comprising nucleosomes, or genomic DNA comprising histones. In some embodiments, transposon sequences can be associated with affinity tags in order to integrate the transposon sequence at a particular sequence in a target nucleic acid. For example, a transposon sequence may be associated with a protein that targets specific nucleic acid sequences, e.g., histones, chromatin-binding proteins, transcription factors, initiation factors, etc., and antibodies or antibody fragments that bind to particular sequence-specific nucleic-acid-binding proteins. In an exemplary embodiment, a transposon sequence is associated with an affinity tag, such as biotin; the affinity tag can be associated with a nucleic-acid-binding protein. In some embodiments, a CE may comprise such target nucleic acid.

It will be understood that during integration of some transposon sequences into a target nucleic acid, several consecutive nucleotides of the target nucleic acid at the integration site are duplicated in the integrated product. Thus the integrated product can include a duplicated sequence at each end of the integrated sequence in the target nucleic acid. As used herein, the term "host tag" or "g-tag" can refer to a target nucleic acid sequence that is duplicated at each end of an integrated transposon sequence. Single-stranded portions of nucleic acids that may be generated by the insertion of transposon sequences can be repaired by a variety of methods well known in the art, for example by using ligases, oligonucleotides and/or polymerases.

In some embodiments, a plurality of the transposon sequences provided herein is inserted into a target nucleic acid. Some embodiments include selecting conditions sufficient to achieve integration of a plurality of transposon sequences into a target nucleic acid such that the average distance between each integrated transposon sequence comprises a certain number of consecutive nucleotides in the target nucleic acid.

Some embodiments include selecting conditions sufficient to achieve insertion of a transposon sequence or sequences into a target nucleic acid, but not into another transposon sequence or sequences. A variety of methods can be used to reduce the likelihood that a transposon sequence inserts into another transposon sequence. Examples of such methods useful with the embodiments provided herein can be found in for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

In some embodiments, conditions may be selected so that the average distance in a target nucleic acid between integrated transposon sequences is at least about 5, 10, 20, 30, 40, 50, 60, 70, 80, 90, 100, or more consecutive nucleotides. In some embodiments, the average distance in a target nucleic acid between integrated transposon sequences is at least about 100, 200, 300, 400, 500, 600, 700, 800, 900, 1000, or more consecutive nucleotides. In some embodiments, the average distance in a target nucleic acid between integrated transposon sequences is at least about 1 kb, 2 kb, 3 kb, 4 kb, 5 kb, 6 kb, 7 kb, 8 kb, 90 kb, 100 kb, or more consecutive nucleotides. In some embodiments, the average distance in a target nucleic acid between integrated transposon sequences is at least about 100 kb, 200 kb, 300 kb, 400 kb, 500 kb, 600 kb, 700 kb, 800 kb, 900 kb, 1000 kb, or more consecutive nucleotides. As will be understood, some conditions that may be selected include contacting a target nucleic acid with a certain number of transposon sequences.

Some embodiments of the methods described herein include selecting conditions sufficient to achieve integration of at least a portion of transposon sequences into a target nucleic acid that are different. In preferred embodiments of the methods and compositions described herein, each transposon sequence integrated into a target nucleic acid is different. Some conditions that may be selected to achieve integration of a certain portion of transposon sequences into target sequences that are different include selecting the degree of diversity of the population of transposon sequences. As will be understood, the diversity of transposon sequences arises in part due to the diversity of the barcodes of such transposon sequences. Accordingly, some embodiments include providing a population of transposon sequences in which at least a portion of the barcodes are different. In some embodiments, at least about 10%, 20%, 30%, 40%, 50%, 60%, 70%, 80%, 90%, 95%, 98%, 99%, or 100% of barcodes in a population of transposon sequences are different. In some embodiments, at least a portion of the transposon sequences integrated into a target nucleic acid are the same.

Some embodiments of preparing a template nucleic acid can include copying the sequences comprising the target nucleic acid. For example, some embodiments include hybridizing a primer to a primer site of a transposon sequence integrated into the target nucleic acid. In some such embodiments, the primer can be hybridized to the primer site and extended. The copied sequences can include at least one barcode sequence and at least a portion of the target nucleic acid. In some embodiments, the copied sequences can include a first barcode sequence, a second barcode sequence, and at least a portion of a target nucleic acid disposed therebetween. In some embodiments, at least one copied nucleic acid can include at least a first barcode sequence of a first copied nucleic acid that can be identified or designated to be paired with a second barcode sequence of a second copied nucleic acid. In some embodiments, the primer can include a sequencing primer. In some embodiments sequencing data is obtained using the sequencing primer. In more embodiments, adaptors comprising primer sites can be ligated to each end of a nucleic acid, and the nucleic amplified from such primer sites.

Some embodiments of preparing a template nucleic acid can include amplifying sequences comprising at least a portion of one or more transposon sequences and at least a portion of a target nucleic acid. In some embodiments, at least a portion of a target nucleic acid can be amplified using primers that hybridize to primer sites of integrated transposon sequences integrated into a target nucleic acid. In some such embodiments, an amplified nucleic acid can include a first barcode sequence, and second barcode sequence having at least a portion of the target nucleic acid disposed therebetween. In some embodiments, at least one amplified nucleic acid can include at least a first barcode sequence of a first amplified nucleic acid that can be identified to be paired with a second barcode sequence of a second amplified sequence.

Some methods of preparing template nucleic acids include inserting transposon sequences comprising single-stranded linkers. In one example transposon sequences (ME-P1-linker-P2-ME; mosaic end-primer site 1-linker-primer site 2-mosaic end) are inserted into a target nucleic acid. The target nucleic acid having the inserted transposon/linker sequences can be extended and amplified.

In one embodiment of the compositions and methods described herein, transposomes are used that have symmetrical transposable end sequences to produce an end-tagged target nucleic acid fragment (tagmented fragment or tagment). Each tagmented fragment therefore contains identical ends, lacking directionality. A single primer PCR, using the transposon end sequences, can then be employed to amplify the template copy number from 2n to $2n*2^x$ where x corresponds to the number of PCR cycles. In a subsequent step, PCR with primers can add additional sequences, such as sequencing adapter sequences.

In some embodiments, it can be advantageous for each template nucleic acid to incorporate at least one universal primer site. For example, a template nucleic acid can include first end sequences that comprise a first universal primer site, and second end sequences that comprise a second universal primer site. Universal primer sites can have various applications, such as use in amplifying, sequencing, and/or identifying one or more template nucleic acids. The first and second universal primer sites can be the same, substantially similar, similar, or different. Universal primer sites can be introduced into nucleic acids by various methods well known in the art, for example, ligation of primer sites to nucleic acids, amplification of nucleic acids using tailed primers, and insertion of a transposon sequence comprising a universal primer site.

Transposomes

A "transposome" comprises an integration enzyme such as an integrase or transposase, and a nucleic acid comprising an integration recognition site, such as a transposase recognition site. In embodiments provided herein, the transposase can form a functional complex with a transposase recognition site that is capable of catalyzing a transposition reaction. The transposase may bind to the transposase recognition site and insert the transposase recognition site into a target nucleic acid within CE in a process sometimes termed "tagmentation". In some such insertion events, one strand of the transposase recognition site may be transferred into the target nucleic acid. In one example, a transposome comprises a dimeric transposase comprising two subunits, and two non-contiguous transposon sequences. In another example, a transposase comprises a dimeric transposase comprising two subunits, and a contiguous transposon sequence.

Some embodiments can include the use of a hyperactive Tn5 transposase and a Tn5-type transposase recognition site (Goryshin and Reznikoff, *J. Biol. Chem.*, 273:7367 (1998)), or MuA transposase and a Mu transposase recognition site comprising R1 and R2 end sequences (Mizuuchi, K., *Cell*, 35: 785, 1983; Savilahti, H, et al., *EMBO J.*, 14: 4893, 1995). ME sequences can also be used as optimized by a skilled artisan. The above references are incorporated herein by reference.

More examples of transposition systems that can be used with certain embodiments of the compositions and methods provided herein include *Staphylococcus aureus* Tn552 (Colegio et al., *J. Bacteriol.*, 183: 2384-8, 2001; Kirby C et al., *Mol. Microbiol.*, 43: 173-86, 2002), Ty1 (Devine & Boeke, *Nucleic Acids Res.*, 22: 3765-72, 1994 and International Publication WO 95/23875), Transposon Tn7 (Craig, N L, *Science*. 271: 1512, 1996; Craig, N L, Review in: *Curr Top Microbiol Immunol.*, 204:27-48, 1996), Tn/O and IS10 (Kleckner N, et al., *Curr Top Microbiol Immunol.*, 204:49-82, 1996), Mariner transposase (Lampe D J, et al., *EMBO J.*, 15: 5470-9, 1996), Tc1 (Plasterk R H, *Curr. Topics Microbiol. Immunol.*, 204: 125-43, 1996), P Element (Gloor, G B, *Methods Mol. Biol.*, 260: 97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204: 1-26, 1996), retroviruses (Brown, et al., *Proc Natl Acad Sci USA*, 86:2525-9, 1989), and retrotransposon of yeast (Boeke & Corces, *Annu Rev Microbiol.* 43:403-34, 1989). More examples include IS5, Tn10, Tn903, IS911, and engineered versions of transposase family enzymes (Zhang et al., (2009) *PLoS Genet.* 5:e1000689. Epub 2009 Oct. 16; Wilson C. et al (2007) *J. Microbiol. Methods* 71:332-5). The above references are incorporated herein by reference.

More examples of integrases that may be used with the methods and compositions provided herein include retroviral integrases and integrase recognition sequences for such retroviral integrases, such as integrases from HIV-1, HIV-2, SIV, PFV-1, RSV.

Transposon Sequences

Some embodiments of the compositions and methods provided herein include transposon sequences. In some embodiments, a transposon sequence includes at least one transposase recognition site. In some embodiments, a transposon sequence includes at least one transposase recognition site and at least one barcode. Transposon sequences useful with the methods and compositions provided herein are provided in U.S. Patent Application Pub. No. 2012/0208705, U.S. Patent Application Pub. No. 2012/0208724 and Int. Patent Application Pub. No. WO 2012/061832, each of which is incorporated by reference in its entirety. In some embodiments, a transposon sequence includes a first transposase recognition site, a second transposase recognition site, and a barcode disposed therebetween.

Transposomes with Non-Contiguous Transposon Sequences

Some transposomes provided herein include a transposase comprising two transposon sequences. In some such embodiments, the two transposon sequences are not linked to one another, in other words, the transposon sequences are non-contiguous with one another. Examples of such transposomes are known in the art, see e.g., U.S. Patent Application Pub. No. 2010/0120098, the disclosure of which is incorporated herein by reference in its entirety.

Looped Structures

In some embodiments, a transposome comprises a transposon sequence nucleic acid that binds two transposase subunits to form a "looped complex" or a "looped transposome." In one example, a transposome comprises a dimeric transposase and a transposon sequence. Looped complexes can ensure that transposons are inserted into target DNA while maintaining ordering information of the original target DNA and without fragmenting the target DNA. As will be appreciated, looped structures may insert primers, barcodes, indexes and the like into a target nucleic acid, while maintaining physical connectivity of the target nucleic acid. In some embodiments, the CE may comprise the target nucleic acid. In some embodiments, the transposon sequence of a looped transposome can include a fragmentation site such that the transposon sequence can be fragmented to create a transposome comprising two transposon sequences. Such transposomes are useful to ensuring that neighboring target DNA fragments, in which the transposons insert, receive code combinations that can be unambiguously assembled at a later stage of the assay.

Certain Methods of Making Transposon Sequences

The transposon sequences provided herein can be prepared by a variety of methods. Exemplary methods include direct synthesis and hairpin extension methods. In some embodiments, transposon sequences may be prepared by direct synthesis. For example, a transposon sequence comprising a nucleic acid may be prepared by methods comprising chemical synthesis. Such methods are well known in the art, e.g., solid phase synthesis using phosphoramidite precursors such as those derived from protected 2'-deoxynucleosides, ribonucleosides, or nucleoside analogues. Example methods of preparing transposon sequencing can be found in, for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

In some embodiments comprising looped transposomes, transposon sequences comprising a single stranded linker can be prepared. In some embodiments, the linker couples the transposon sequences of a transposome such that a transposon sequence comprising a first transposase recognition sequence is coupled to a second transposon sequence comprising a second transposase recognition sequence in a 5' to 3' orientation. In some embodiments, the linker couples a transposon sequence comprising a first transposase recognition sequence to a second transposon sequence comprising a second transposase recognition sequence in a 5' to 5' orientation or in a 3' to 3' orientation. Coupling transposon sequences of a transposome in either a 5' to 5' orientation or in a 3' to 3' orientation can be advantageous to prevent transposase recognition elements, in particular mosaic elements (ME or M), from interacting with one another. Coupled transposon sequences can be prepared by preparing transposon sequences comprising either an aldehyde group or oxyamine group. The aldehyde and oxyamine groups can interact to form a covalent bond thus coupling the transposon sequences.

In some embodiments, transposomes comprising complementary sequences can be prepared. In one embodiment, a transposase is loaded with transposon sequences comprising complementary tails. The tails hybridize to form a linked transposon sequence. Hybridization may occur in dilute conditions to decrease the likelihood of hybridization between transposomes.

Targeted Insertion

In some embodiments of the methods and compositions provided herein, transposon sequences may be inserted at particular targeted sequences of a target nucleic acid.

Transposition into dsDNA can be more efficient than into ssDNA targets. In some embodiments, dsDNA is denatured into ssDNA and annealed with oligonucleotide probes (20-200 bases). These probes create sites of dsDNA that can be efficiently used as integration sites with transposomes provided herein. In some embodiments, dsDNA can be targeted using D-loop formation with recA-coated oligo probes, and subsequent triplex formation. In some such embodiments, the D-loop is a preferred substrate for transposomes comprising Tn4430 transposase. In more embodiments, regions of interest in dsDNA can be targeted using sequence-specific DNA binding proteins such as zinc-finger complexes, and other affinity ligands to specific DNA regions.

In some embodiments, transposomes comprising a transposase having a preferred substrate of mismatched positions in a target nucleic acid may be used to target insertion into the target nucleic acid. For example, some MuA transposases, such as HYPERMU (Epicenter), have a preference for mismatched targets. In some such embodiments, oligonucleotide probes comprising a mismatch are annealed to a single-stranded target nucleic acid. Transposomes comprising MuA transposases, such as HYPERMU, can be used to target the mismatched sequences of the target nucleic acid.

Contiguity Preserving Element (CE)

A contiguity preserving element (CE) is a physical entity which preserves at least two, or more, or all analytes in close proximity (or contiguity) through one or more assay steps and provides access to assay reagents and can be pooled and split multiple times without losing the proximity of the analytes.

In some embodiments, the CE can be a solid support. In one embodiment, the CE may be an emulsion or droplet. In some embodiments, the CE is gel, hydrogel, or gel bead. In some embodiments, the CE may comprise a solid support such as beads. In some embodiments, the beads may further comprise antibodies, oligonucleotides, and/or barcodes. In another embodiment, the CE may constitute a DNA nanoball created by WGA, RCA, or condensation of any nucleic acid reagent.

In some embodiments, a CE can be made by embedding the nucleic acid from cells or from a single cell, or the amplification product thereof (from WGA, etc.) in a polymer matrix such as agarose, polyacrylamide, alginate, etc. In some embodiments, the contiguity of the contents of the cells or of a single cell within a CE are maintained by preserving physical proximity of the components to one another through encapsulation (such as in a polymer matrix), immobilization on a bead or entrapment, effectively maintaining contiguity information within the CE through repeated rounds of pooling and redistribution. The feature that a collection of CE can be independently pooled and split, reacted with assay reagents, pooled and split again, etc. yet maintaining the contiguity of the analytes constituting an individual CE enables the combinatorial indexing through different split and pool steps.

In some embodiments, the analytes in the contiguity preserving element are accessible to assay reagents including aqueous solutions, enzymes (e.g., fragmentases, polymerases, ligases, transposases, kinases, restriction endonucleases, proteases, phosphatases, lipases), nucleic acid adapters, nucleic acid barcodes, labels.

In some embodiments, the CE comprises cells or a single cell. In some embodiments, the CE comprises nucleic acid from cells or from a single cell, such as DNA, mRNA, or cDNA; macromolecules of cells or of a single cell including proteins, polysaccharides, lipids, and nucleic acids, as well as small molecules such as primary metabolites, secondary metabolites, and natural products from cells or from a single cell. In some embodiments, the nucleic acid undergoes amplification such as, PCR or whole genome amplification before forming the CE comprising the nucleic acid. In some embodiments, analysis of the DNA and mRNA can be performed in parallel.

In some embodiments, one or more analytes of a CE is labeled with one or more labels. Exemplary labels include but are not limited to DNA barcodes or indices, fluorescent labels, chemiluminescent labels, RNA barcodes or indices, radioactive labels, antibody comprising a label, beads comprising a label.

In some embodiments, a method can include the steps of (a) compartmentalizing the CE comprising target nucleic acid into a plurality of first vessels; (b) providing a first index to the target nucleic acid of each first vessel, thereby obtaining a first indexed nucleic acid; (c) combining the first indexed nucleic acids; (d) compartmentalizing the first indexed template nucleic acids into a plurality of second vessels; (e) providing a second index to the first indexed template nucleic acid of each second vessel, thereby obtaining a second indexed nucleic acid. The steps a-e can be continued with additional cycles of one or more steps from the a-e series to derive additional virtual compartments. This method of combinatorial indexing can be used to effectively create a large number of virtual compartments from a limited number of physical compartments.

In some embodiments, a method can include the steps of (a) providing a CE comprising non-nucleic acid analytes (e.g. proteins) with attached nucleic acid reporters; (b) compartmentalizing the CE into a plurality of first vessels; (c) providing a first index to the target nucleic acid reporters of each first vessel, thereby obtaining a first indexed target nucleic acid reporter; (c) combining the first indexed nucleic acid reporters; (d) compartmentalizing the first indexed CEs into a plurality of second vessels; (e) providing a second index to the first indexed nucleic acid reporters of each second vessel, thereby obtaining a second indexed nucleic acid reporter. The steps a-e can be continued with additional cycles of one or more steps from the a-e series to derive additional virtual compartments. The compartmentalization step can further include nucleic acid amplification or capture step such as PLA, PEA or other technique that captures or amplifies nucleic acids.

In some embodiments, a formalin-fixed, paraffin embedded tissue can be divided into sections, with each section added to a CE. Each CE can be subsequently analyzed for content or sequence and at a later stage a 2D or 3D map can be obtained of the content of each slide.

In some embodiments, a nucleic acid or nucleic acids can be embedded in a matrix that confines the nucleic acids to a defined space but allows reagent access to perform steps including, but not limited to, amplification (PCR, whole-genome amplification, random primer extension, etc.), ligation, transposition, hybridization, restriction digestion and DNA mutagenesis. Examples of mutagenesis include, but are not limited to, error-prone extension, alkylation, bisulfite conversion, and activation-induced (cytidine) deaminases, etc.

In some embodiments, methods and compositions that use CEs can be combined together with mutagenic assembly approaches to greatly improve assembly of DNA sequence information. Genomic DNA can be fragmented and partitioned into plurality of CEs, with each CE comprising a fraction of the genome. Different fractions of the genome receive different barcodes, allowing fractions of the genome to be assembled independently. One of the larger challenges is the assembly of repeats. One method to assemble repeats is outlined by Levy, D. and Wigler, M. (2014) Facilitated sequence counting and assembly by template mutagenesis. Proc. of the Natl. Acad. Sci., 111 (43). E4632-E4637. ISSN 0027-8424. Assembly approaches are also discussed in US20140024537, titled: Methods And Systems for Determining Haplotypes And Phasing of Haplotypes and this application is incorporated by reference in its entirety. The above references are incorporated herein by reference.

For methods that combine partitioning of DNA fragments with a mutagenesis or related approach partitioning can be performed with CE, wells, indexes, virtual indexes, physical compartments, droplets etc. Mutagenesis can be performed by several methods including but are not limited to error-prone extension, alkylation, bisulfite conversion, and activation-induced (cytidine) deaminases, etc. The method of partitioning nucleic acid into CEs and mutagenesis approach can be useful where conventional methods make it challenging to assemble repeats or difficult regions.

In some embodiments, the methods set forth herein can be used for variant phasing, (de novo) genome assembly, screening populations of cells to determine heterogeneity across the population and determine cell-to-cell differences.

In some embodiments, cDNA from cells or from a single cell is isolated in vessels and converted to a CE that is indexed through the virtual compartmentalization approach as described above. This enables gene expression and transcript profiling from 1000's, 10,000's, 100,000's and even greater number of different indexed single cell libraries.

In some embodiments, the number of single cells that can be analyzed is approximately 10% of the total number of virtual compartments due to Poisson sampling. For a four tier indexing scheme with 96-well compartments at each step, a total of $10\% \times 96 \times 96 \times 96 \times 96 =$ over 8 million single cells can be analyzed in one experiment using a total of $4 \times 96 = 384$ physical compartments. In the example of FIG. 3, four combinatoric dilution and pooling steps are used to create a large number of virtual compartments (a set of molecules or DNA library elements containing a unique index combination). In this example, the contiguous DNA vessel is created by encapsulation of the contents of a single cell in a polymer matrix (e.g. PAM=polyacrylamide). In preferred particular embodiment for genomic analysis, the genomic DNA contents of the single cell are amplified by MDA (a WGA multiple displacement amplification reaction). This single cell MDA product constitutes the DNA vessel that proceeds through the combinatoric indexing scheme. For gene expression, a single cell cDNA preparation can be made from the single cell vessel as described by Picelli (Picelli, 2014). In the preferred embodiment, the initial indexes are attached to the genomic DNA or cDNA through standard library preparation techniques using fragmentation (enzymatic) and adapter ligation, or through tagmentation using transposase complexes. In the preferred embodiment, subsequent indexes are attached to the library via ligation or PCR. Ligation is preferred since it is easy to add indexed adapters in a sequential fashion. The final step may involve just indexed PCR or ligation and PCR.

In some embodiments, the target nucleic acid is histone/protein-protected (see Buenrostro et al. Nature Methods 10, 1213-1218 (2013) doi:10.1038/nmeth.2688, incorporated herein by reference). Applications include epigenomic profiling, and the analysis of open chromatin and DNA-binding proteins and nucleosome position.

In some embodiments, contiguity preserving elements may comprise a single cell and the nucleic acid from the cell may be amplified. Subsequently, each contiguity preserving element can be uniquely indexed through the combinatorial indexing scheme. Short sequencing reads can be grouped based on unique index. Long synthetic reads can be individually de novo assembled based on unique index (McCoy et al. Plosone 2014 (DOI: 10.1371/journal.pone.0106689) Illumina TruSeq Synthetic Long-Reads Empower De Novo Assembly and Resolve Complex, Highly-Repetitive Transposable Elements, incorporated herein by reference)

In some embodiments, CE may comprise contents of a cell, for example, proteins, organelles, RNA, DNA, ribosomes, antibodies, steroids, specialized structures, glycans, lipids, small molecules, molecules that may affect a biological pathway, mono and polysaccharides, alkaloids, primary and secondary metabolites.

In some embodiments, the organelles within the CE may be differentially stained. Examples of organelle staining reagents are organelle targeted fluorescent proteins (Cellular Lights™), classic organelle stains or dye conjugates that selectively or non-selectively can label organelles or cell structures.

In some embodiments, an analyte of interest in a CE is a protein. Proteins can be labeled with barcodes or alternative labels. The barcode or labels can be read out using traditional arrays or sequence-based methods. Proximity ligation approaches and antibody-index sequences can be used to detect proteins (Fredriksson et al. Nature Biotechnology 20, 473-477 (2002), incorporated herein by reference) together with the detection of the barcode sequences to establish identity and abundance of the proteins in each individual cell. Proteins can be labeled by various methods (www.piercenet.com/cat/protein-antibody-labeling) known by a skilled worker including in vivo and in vitro site-specific chemical labeling strategies.

Proximity ligation (Duo-link PLA, www.sigmaaldrich.com/life-science/molecular-biology/molecular-biology-products.html?TablePage=112232138, Multiplexed proximity ligation assay EP 2714925 A1) is an example for the detection of proteins, protein-protein interactions, and post-translational modifications that can be adapted for use in a contiguity preserving element. This method can be used to detect, and quantify a specific protein or protein complex in a contiguity preserving element. One example of a workflow is the following: (1) make contiguity preserving element or elements, (2) wash and add a pair or pairs of primary antibodies specific to the protein of interest, (3) wash and stain with barcode-labeled antibodies. Each population of contiguity preserving elements in a vessel receives a different barcode labeled antibody. Through proximity ligation the pair or pairs of primary antibodies, amplifiable products can be formed that contain a unique barcode for a specific protein. One barcode can be specific for the protein of interest, while other barcodes are used to assign the protein to a specific contiguity preserving element and or cell. Through one or more split-and-pool steps, fractions can be differentially labeled. As such, the content of individual contiguity preserving elements can be analyzed without the need to process each contiguity preserving elements individually in many parallel steps. It is particularly a great advantage to process 10, 100, 1000, 10,000, 100,000, 1,000,000, 10,000,000. 100,000,000 and more contiguity preserving elements in such a manner. Steroids and small molecules can be detected in a similar manner as described for proteins. Barcode labeled antibodies can be developed for steroids (Hum Reprod. 1988 January; 3(1):63-8. Antibodies against steroids. Bösze P et al. Alternatively, fluorescent dye and radioactive conjugates have been described (www.jenabioscience.com/cms/en/1/catalog/2305_fluorescent_hormones.html). These antibody conjugates for steroids can be processed as described above. Various methods can be used to detect one or more components of the contiguity preserving element. One or more components of the contiguity preserving element can be labeled with chemi-luminescent, fluorescent, radioactive probes, DNA-tags, barcodes, and indices. Amplification strategies can be utilized to enhance the signal. For example, rolling circle amplification (RCA) can be used to detect analytes. RCA products can subsequently be detected by sequencing, fluorescent decoders (probes). Additionally, microarrays, protein arrays, sequencing, nano-pore sequencing, next-generation sequencing, capillary-electrophoresis, bead-arrays can be used for readout.

Establishing Contiguity of the Contents of a Cell

In some embodiments, the contiguity of the content of cells or from a single cell, for example but not limited to DNA, RNA, protein, organelles, metabolites, small molecules can be preserved in a contiguity preserving element (CE). A CE may be created by several methods including but not limited to encapsulating the contents within a droplet, embedding the contents in a polymer matrix (after encapsulation), and attachment of the contents to a bead. In the preferred embodiment, the CE is permeable to assay reagents such as aqueous buffers, enzymes (polymerases, ligases, transposases, etc.), nucleotides, oligonucleotide adapters, transposons, and primers, etc. Indexed libraries are created from this CE as described above. Repeated rounds of dilution into physical compartments, attachment of compartment specific indexes, pooling and redilution into additional compartments leads to an exponential creation of many virtual compartments. If designed appropriately, the contents of each CE, in the end, will be virtually indexed with a unique barcode. As an example in FIG. 1, a four tier indexing scheme leads to a large number of virtual compartments and indexes (>84 million) with just 4×96=384 total physical compartments. In the preferred embodiment, compartment-specific indexes are added at each compartmentalization tier via tagmentation, ligation, or PCR. In the preferred embodiment, each physical compartment at each step has a unique index. Subsequent compartmentalization can use the same or different indexes. If the same indexes are used from one compartmentalization tier to the next, the position of the index within the final sequence string will identify the compartment and the compartmentalization tier.

Analysis of Cellular Components Using Droplets

In one embodiment, the CE may be an emulsion or droplet. In one embodiment, the CE is a droplet in contact with oil. In one example, CE comprising nucleic acid includes the dilution and partitioning of a nucleic acid sample into droplets, compartments, or beads. In one embodiment, the droplet comprises cells or a single cell. In one embodiment, the CE comprising single cells includes the dilution and partitioning of a single cell into droplets, compartments, or beads.

In some embodiments, a "Droplet" can be a volume of liquid on a droplet actuator which is at least partially bounded by filler fluid. For example, a droplet may be completely surrounded by filler fluid or may be bounded by filler fluid and one or more surfaces of a droplet actuator. Droplets may take a wide variety of shapes; non-limiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

Droplet actuators are used to conduct a wide variety of droplet operations. A droplet actuator typically includes two substrates separated by a space. The substrates include electrodes for conducting droplet operations. The space is typically filled with a filler fluid that is immiscible with the fluid that is to be manipulated on the droplet actuator. Surfaces exposed to the space are typically hydrophobic. Analysis of genetic material (genomics) and its expression (functional genomics), proteomics, combinatorial library analysis, and other multiplexed bioanalytical applications can be performed in droplets and the following operations can be carried out on the analysis droplet actuator. Methods of manipulating droplets using droplet actuator are disclosed in US Application Publications 20100130369 and 20130203606 respectively, each of which is incorporated herein by reference.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S. Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define on-actuator dispensing reservoirs. The spacer height may, for example, be at least about 5 µm, 100 µm, 200 µm, 250 µm, 275 µm or more. Alternatively or additionally the spacer height may be at most about 600 µm, 400 µm, 350 µm, 300 µm, or less. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and opto-electrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD. In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PRO-BIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.). Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1×-, 2×-3×-droplets are usefully controlled operated using 1, 2, and 3 electrodes, respectively. If the droplet footprint is greater than number of electrodes available for conducting a droplet operation at a given time, the difference between the droplet size and the number of electrodes should typically not be greater than 1; in other words, a 2× droplet is usefully controlled using 1 electrode and a 3× droplet is usefully controlled using 2 electrodes. When droplets include beads, it is useful for droplet size to be equal to the number of electrodes controlling the droplet, e.g., transporting the droplet.

In some aspects, a nucleic acid library can be prepared from cells or a single cell using CEs such as droplets. In some embodiments, cells may be suspended in a buffer. In some embodiments, the cell suspension may be introduced to a droplet actuator. Using electrode mediated droplet operations array of droplets comprising cell suspension may be dispensed such that each droplet comprises a single cell. Using electrode mediated droplet operations, array of reagent droplets comprising cell lysis buffer may be dispensed (lysis buffer droplets). The lysis buffer droplets and the array of cell suspension droplets comprising single cells can be combined using electrode mediated operations to form a cell lysate droplet such that the cell lysate droplet comprise components of the single cells. Reaction reagents comprising unique nucleic acid barcodes, transposons and suitable enzymes (e.g., fragmentases, polymerases, ligases, transposases, reverse transcriptases etc.) may be introduced to a droplet actuator. In some embodiments, the transposons and/or the barcodes may comprise primer binding sites. Using electrode mediated droplet operations an array of reagent droplets comprising reaction reagents may be dispensed such that each reagent droplet comprises unique nucleic acid barcodes and suitable enzymes. The cell lysate droplets and the reagent droplets can be combined using electrode mediated operations to form an array of first barcoded droplet in which the nucleic acid from a single cell are acted upon by the enzymes from the reagent droplets such that the nucleic acids comprise a barcode. In some embodiments, the mRNA within the cell lysate droplets can be reverse transcribed when cell lysate droplets and the reagent droplets are combined and the cDNA can comprise barcodes. In some embodiments, the barcodes can comprise primer binding sites and unique molecular indices. Using electrode mediated droplet operations, the first barcoded droplet can be further combined multiple times with reagent droplets to generate arrays of second barcode droplets, third barcode droplets etc. In some embodiments, for each round of combination, the barcodes are different. Thus multiple rounds of combining the barcode droplets with reagent droplets will generate combinatorial barcoding. At the end the nucleic acid from the different droplets can be pooled and sequenced. The sequencing information can reveal sequencing information of the nucleic acid from the cell, and optionally also identify the source of the nucleic acids (e.g. cells or a single cell). Such information is valuable if the nucleic acid comprises a mutation associated with a disease such as inherited genetic disease, or cancer.

In some aspects, the methods of the present application can be applied for proteomics. An array of bead containing droplets can be made by introducing beads suspension to a droplet actuator to dispense an array of droplets from the bead suspension such that each droplet in the array of droplets comprise a single bead (see US Application Publication 20100130369, incorporated herein by reference). The beads can comprise antibodies or other affinity probes (see Immobilized Biomolecules in Analysis. A Practical Approach. Cass T, Ligler F S, eds. Oxford University Press, New York, 1998. pp 1-14, incorporated herein by reference, for typical attachment protocols). In some embodiments, the antibodies can be specific for cell surface epitopes. In some embodiments, the antibodies can be monoclonal and in other embodiments, the antibodies can be polyclonal. Using electrode mediated droplet operations, an array of bead suspension droplets may be combined with an array of droplets comprising single cells to yield an array of cell on bead droplets such that the antibodies on the beads bind to the cell surface proteins. In some embodiments, the antibodies can be specific for protein inside a cell. Using electrode mediated droplet operations, an array of bead suspension droplets may be combined with an array of droplets comprising single cell lysates such that the antibodies on the beads bind to the proteins within a cell to yield an array of protein on bead droplets. Optionally, using electrode mediated droplet operations, the array of protein on bead droplets can be combined with an array of reagent droplets comprising protein labeling reagents such that proteins can be uniquely labeled. The bound proteins can be detected from the labels associated or by other means (SDS-polyacrylamide gel electrophoresis, ELISA etc.). The identity of the protein and the source of the protein can be determined. In some embodiments, the proteomic data can be correlated with sequencing data.

In some embodiments, the antibodies may be specific for other biomolecules and not limited to a protein. Such biomolecules may include but are not limited to polysaccharides or lipids. In some embodiments, identity and the source of such biomolecules can be correlated with the sequence data generated above.

In Situ Cellular Analysis

In some embodiments, cells and their components can be analyzed in situ. In some embodiments, cells may be allowed to pass through a flow cell.

As used herein, the term "flow cell" is intended to mean a chamber having a surface across which one or more fluid reagents can be flowed. Generally, a flow cell will have an ingress opening and an egress opening to facilitate flow of fluid. Examples of flowcells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

In some embodiments, flow cells may house arrays. Arrays used for nucleic acid sequencing often have random spatial patterns of nucleic acid features. For example, HiSeq™ or MiSeq™ sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Exemplary patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The features of such patterned arrays can be used to capture a single nucleic acid template molecule to seed subsequent formation of a homogenous colony, for example, via bridge amplification. Such patterned arrays are particularly useful for nucleic acid sequencing applications.

In some embodiments, the flow cell surface may comprise capture moieties such as antibodies to immobilize the cells passing through it on the flow cell surface. In some embodiments, the antibodies on the flow cell surface may bind specifically to cell surface proteins. In some embodiments, the antibodies may bind specifically to cell surface proteins of cancerous cells, thus enriching cancerous cells on flow cell surface.

In some embodiments, the cells can be sorted into various types by cell sorting technology known in the art before passing the cells into the flow cell. Exemplary cell sorting technology include but are not limited to Fluorescent Activated Cell Sorting, or FACS which utilizes flow cytometry, Magnetic-activated cell sorting (MACS) (Miltenyi Biotec Inc., San Diego, Calif.), or by column-free cell separation technique in which a tube of labeled cells is placed inside a magnetic field. Positively selected cells are retained in the tube while negatively selected cells are in the liquid suspension (STEMCELL Technologies Inc., Vancouver, BC, Canada).

In some embodiments, the cells passing through the flow cell may be lysed within the flow cell and thus releasing the nucleic acid of the cells (DNA and RNA) in the flow cell. In some embodiments, the cells are immobilized on the flow cell prior to lysis. Methods of cell lysis are known in the art which include but not limited to sonication, protease treatment, by osmotic shock, high salt treatment. In some embodiments, the entire RNA can be reverse transcribed. In some embodiments, unique barcodes can be introduced to the nucleic acid from the cells, for example the DNA, RNA, or cDNA. Methods of introducing barcodes into a nucleic acid are discussed above and include but are not limited to tagmentation using Nextera™ technology, ligases, polymerases. In some embodiments, the barcodes can be useful for identification of the cell source. In some embodiments, the barcodes may have primer binding sites. In some embodiments multiple barcodes may be introduced into the nucleic acid. In some embodiments, the multiple barcodes are different from each other. In some embodiments, the nucleic acid with barcodes may be diffused; pooled again and additional barcodes may be introduced. In some embodiments, following or during the introduction of the barcodes, the nucleic acid can be fragmented. In some embodiments, the fragmented nucleic acid may be amplified prior to diffusing in the flow cell. In some embodiments, the fragmented nucleic acid comprising the barcodes may be diffused to a different part of the flow cell comprising capture probes and immobilized on the flow cell. In some embodiments, the immobilized fragmented nucleic acid may be subjected to bridge amplification.

In some embodiments of the above aspects, the cell passing through the flow cell is a single cell. In some embodiments, the entire transcriptome can be evaluated. In some embodiments, the DNA and the RNA from cells or from a single cell can be evaluated simultaneously for the sequence information. In some embodiments, the proteins from cells or from a single cell can be evaluated for identity and for sequence information. In some embodiments, other analytes from cells or from a single cell such as, lipids, carbohydrates, cellular organelles can be evaluated.

Fragmenting Template Nucleic Acids

Some embodiments of preparing a template nucleic acid can include fragmenting a target nucleic acid. In some embodiments, barcoded or indexed adapters are attached to the fragmented target nucleic acid. Adapters can be attached using any number of methods well known in the art such as ligation (enzymatic or chemical), tagmentation, polymerase extension, and so forth. In some embodiments, insertion of transposomes comprising non-contiguous transposon sequences can result in fragmentation of a target nucleic acid. In some embodiments comprising looped transposomes, a target nucleic acid comprising transposon sequences can be fragmented at the fragmentation sites of the transposon sequences. Further examples of method useful to fragment target nucleic acids useful with the embodiments provided herein can be found in for example, U.S. Patent Application Pub. No. 2012/0208705, U.S. Patent Application Pub. No. 2012/0208724 and Int. Patent Application Pub. No. WO 2012/061832, each of which is incorporated by reference in its entirety.

Tagging Single Molecules

The present invention provides methods for tagging molecules so that individual molecules can be tracked and identified. The bulk data can then be deconvoluted and converted back to the individual molecule. The ability to distinguish individual molecules and relate the information back to the molecule of origin is especially important when processes from original molecule to final product change the (stoichiometric) representation of the original population. For example, amplification leads to duplication (e.g., PCR duplicates or biased amplification) that can skew the original representation. This can alter the methylation state call, copy number, allelic ratio due to non-uniform amplification and/or amplification bias. By identifying individual molecules, code-tagging distinguishes between identical molecules after processing. As such, duplications, and amplification bias can be filtered out, allowing accurate determination of the original representation of a molecule or population of molecules.

An advantage of uniquely tagging single molecules is that identical molecules in the original pool become uniquely identified by virtue of their tagging. In further downstream analyses, these uniquely tagged molecules can now be distinguished. This technique can be exploited in assay schemes in which amplification is employed. For example, amplification is known to distort the original representation of a mixed population of molecules. If unique tagging were not employed, the original representation (such as copy number or allelic ratio) would need to account for the biases (known or unknown) for each molecule in the representation. With unique tagging, the representation can accurately be determined by removing duplicates and counting the original representation of molecules, each having a unique tag. Thus, cDNAs can be amplified and sequenced, without fear of bias because the data can be filtered so that only authentic sequences or sequences of interest are selected for further analysis. Accurate reads can be constructed by taking the consensus across many reads with the same barcode.

In some embodiments of the compositions and methods described herein, it is preferred to tag the original population in the early stages of the assay, although tagging can occur at later stages if the earlier steps do not introduce bias or are not important. In any of these applications, the complexity of the barcode sequences should be larger than the number of individual molecules to be tagged. This ensures that different target molecules receive different and unique tags. As such, a pool of random oligonucleotides of a certain length (e.g., 5, 10, 20, 30, 40, 50, 100 or 200 nucleotides in length) is desirable. A random pool of tags represents a large complexity of tags with code space $4^n$ where n is the number of nucleotides. Additional codes (whether designed or random) can be incorporated at different stages to serve as a further check, such as a parity check for error correction.

In one embodiment of the compositions and methods described herein, individual molecules (such as target DNA) are attached to unique labels, such as unique oligo sequences and/or barcodes. Attachment of the labels can occur through ligation, coupling chemistry, adsorption, insertion of transposon sequences, etc. Other means include amplification (such as by PCR, RCA or LCR), copying (such as addition by a polymerase), and non-covalent interactions.

Specific methods comprise including barcodes (e.g., designed or random sequences) to PCR primers so that each template will receive an individual code within the code space, thereby yielding unique amplicons that can be discriminated from other amplicons. This concept can be applied to any method that uses polymerase amplification, such as GoldenGate™ assays and assays disclosed in U.S. Pat. Nos. 7,582,420, 7,955,794, and 8,003,354, each of which is incorporated by reference in its entirety. Code-tagged target sequences can be circularized and amplified by methods such as rolling-circle amplification to yield code-tagged amplicons. Similarly, the code can also be added to RNA Methods of Analyzing Template Nucleic Acids Some embodiments of the technology described herein include methods of analyzing template nucleic acids. In such embodiments, sequencing information can be obtained from template nucleic acids and this information can be used to generate a sequence representation of one or more target nucleic acids.

In some embodiments of the sequencing methods described herein, a linked read strategy may be used. A linked read strategy can include identifying sequencing data that links at least two sequencing reads. For example, a first sequencing read may contain a first marker, and a second sequencing read may contain a second marker. The first and second markers can identify the sequencing data from each sequencing read to be adjacent in a sequence representation of the target nucleic acid. In some embodiments of the compositions and methods described herein, markers can comprise a first barcode sequence and a second barcode sequence in which the first barcode sequence can be paired with the second barcode sequence. In other embodiments, markers can comprise a first host tag and a second host tag. In more embodiments, markers can comprise a first barcode sequence with a first host tag, and a second barcode sequence with a second host tag.

An exemplary embodiment of a method for sequencing a template nucleic acid can comprise the following steps: (a) sequence the first barcode sequence using a sequencing primer hybridizing to the first primer site; and (b) sequence the second barcode sequence using a sequencing primer hybridizing to the second primer. The result is two sequence reads that help link the template nucleic acid to its genomic neighbors. Given long enough reads, and short enough library fragments, these two reads can be merged informatically to make one long read that covers the entire fragment. Using the barcode sequence reads and the 9 nucleotide duplicated sequence present from the insertion, reads can now be linked to their genomic neighbors to form much longer "linked reads" in silico.

As will be understood, a library comprising template nucleic acids can include duplicate nucleic acid fragments. Sequencing duplicate nucleic acid fragments is advantageous in methods that include creating a consensus sequence for duplicate fragments. Such methods can increase the accuracy for providing a consensus sequence for a template nucleic acid and/or library of template nucleic acids.

In some embodiments of the sequencing technology described herein, sequence analysis is performed in real time. For example, real time sequencing can be performed by simultaneously acquiring and analyzing sequencing data. In some embodiments, a sequencing process to obtain sequencing data can be terminated at various points, including after at least a portion of a target nucleic acid sequence data is obtained or before the entire nucleic acid read is sequenced. Exemplary methods, systems, and further embodiments are provided in International Patent Publication No. WO 2010/062913, the disclosure of which is incorporated herein by reference in its entirety.

In an exemplary embodiment of a method for assembling short sequencing reads using a linked read strategy, transposon sequences comprising barcodes are inserted into genomic DNA, a library is prepared and sequencing data is obtained for the library of template nucleic acids. Blocks of templates can be assembled by identifying paired barcodes and then larger contigs are assembled. In one embodiment, the assembled reads can be further assembled into larger contigs through code pairing using overlapping reads.

Some embodiments of the sequencing technology described herein include error detection and correction features. Examples of errors can include errors in base calls during a sequencing process, and errors in assembling fragments into larger contigs. As would be understood, error detection can include detecting the presence or likelihood of errors in a data set, and as such, detecting the location of an error or number of errors may not be required. For error correction, information regarding the location of an error and/or the number of errors in a data set is useful. Methods for error correction are well known in the art. Examples include the use of hamming distances, and the use of a checksum algorithm (See, e.g., U.S. Patent Application Publication No. 2010/0323348; U.S. Pat. Nos. 7,574,305; and 6,654,696, the disclosures of which are incorporated herein by reference in their entireties).

Nested Libraries

An alternative method involves the junction tagging methods above and preparation of nested sequencing libraries. The nested sub-libraries are created from code-tagged DNA fragments. This can allow less frequent transposon tagging across the genome. It can also create a larger diversity of (nested) sequencing reads. These factors can lead to improved coverage and accuracy.

Sub-sampling and whole genome amplification can create many copies of a certain population of starting molecules. DNA fragments are then generated by transposon-specific fragmentation, where each fragment receives a code that allows one to link the fragment back to the original neighbor having a matching code (whether identical, complementary or otherwise informatically linked). The tagged fragments are fragmented at least a second time by random methods or sequence-specific methods, such as enzymatic digestion, random shearing, transposon-based shearing or other methods, thereby creating sub-libraries of the code-tagged DNA fragments. In a useful variation of the previously-described method, code-tagged fragments can be preferentially isolated by using transposons that contain a biotin or other affinity functionality for downstream enrichment purposes. Subsequent library preparation converts the nested DNA fragments into sequencing templates. Paired-end sequencing results in determination of the sequence of the code-tag of the DNA fragments and of the target DNA. Since nested libraries for the same code-tag are created, long DNA fragments can be sequenced with short reads.

Sequencing Methods

The methods and composition described herein can be used in conjunction with a variety of sequencing techniques. In some embodiments, the process to determine the nucleotide sequence of a target nucleic acid can be an automated process.

Some embodiments of the sequencing methods described herein include sequencing by synthesis (SBS) technologies, for example, pyrosequencing techniques. Pyrosequencing detects the release of inorganic pyrophosphate ($PP_i$) as particular nucleotides are incorporated into the nascent strand (Ronaghi et al., *Analytical Biochemistry* 242(1): 84-9 (1996); Ronaghi, M. *Genome Res.* 11(1):3-11 (2001); Ronaghi et al., *Science* 281(5375):363 (1998); U.S. Pat. Nos. 6,210,891; 6,258,568 and 6,274,320, each of which is incorporated by reference in its entirety).

In another example type of SBS, cycle sequencing is accomplished by stepwise addition of reversible terminator nucleotides containing, for example, a cleavable or photobleachable dye label as described, for example, in U.S. Pat. No. 7,427,67, U.S. Pat. No. 7,414,1163 and U.S. Pat. No. 7,057,026, each of which is incorporated by reference in its entirety. This approach, which is being commercialized by Illumina Inc., is also described in International Patent Application Publication Nos. WO 91/06678 and WO 07/123744, each of which is incorporated by reference in its entirety. The availability of fluorescently-labeled terminators, in which both the termination can be reversed and the fluorescent label cleaved, facilitates efficient cyclic reversible termination (CRT) sequencing. Polymerases can also be co-engineered to efficiently incorporate and extend from these modified nucleotides.

Additional exemplary SBS systems and methods which can be utilized with the methods and compositions described herein are described in U.S. Patent Application Publication No. 2007/0166705, U.S. Patent Application Publication No. 2006/0188901, U.S. Pat. No. 7,057,026, U.S. Patent Application Publication No. 2006/0240439, U.S. Patent Application Publication No. 2006/0281109, PCT Publication No. WO 05/065814, U.S. Patent Application Publication No. 2005/0100900, PCT Publication No. WO 06/064199 and PCT Publication No. WO 07/010251, each of which is incorporated by reference in its entirety.

Some embodiments of the sequencing technology described herein can utilize sequencing by ligation techniques. Such techniques utilize DNA ligase to incorporate nucleotides and identify the incorporation of such nucleotides. Exemplary SBS systems and methods which can be utilized with the compositions and methods described herein are described in U.S. Pat. Nos. 6,969,488, 6,172,218, and 6,306,597, each of which is incorporated by reference in its entirety.

The sequencing methods described herein can be advantageously carried out in multiplex formats such that multiple different target nucleic acids are manipulated simultaneously. In particular embodiments, different target nucleic acids can be treated in a common reaction vessel or on a surface of a particular substrate. This allows convenient delivery of sequencing reagents, removal of unreacted reagents and detection of incorporation events in a multiplex manner. In embodiments using surface-bound target nucleic acids, the target nucleic acids can be in an array format. In an array format, the target nucleic acids can be typically coupled to a surface in a spatially distinguishable manner. For example, the target nucleic acids can be bound by direct covalent attachment, attachment to a bead or other particle or associated with a polymerase or other molecule that is attached to the surface. The array can include a single copy of a target nucleic acid at each site (also referred to as a feature) or multiple copies having the same sequence can be present at each site or feature. Multiple copies can be produced by amplification methods such as, bridge amplification or emulsion PCR as described in further detail herein.

The methods set forth herein can use arrays having features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, $10^7$ features/cm$^2$, $5\times10^7$ features/cm$^2$, $10^8$ features/cm$^2$, $5\times10^8$ features/cm$^2$, $10^9$ features/cm$^2$, $5\times10^9$ features/cm$^2$, or higher.

Methods for Reducing Error Rates in Sequencing Data

Some embodiments of the methods and compositions provided herein include reducing the error rates in sequencing data. In some such embodiments, the sense and antisense strands of a double-stranded target nucleic acid are each associated with a different barcode. Each strand is amplified, sequence information is obtained from multiple copies of the amplified strands, and a consensus sequence representation of the Target nucleic acid is generated from the redundant sequence information. Thus, sequence information can originate and be identified from each strand. Accordingly, sequence errors can be identified and reduced where sequence information originating from one strand is inconsistent with sequence information from the other strand.

In some embodiments, the sense and antisense strands of a target nucleic acid are associated with a different barcode. The barcodes may be associated with the target nucleic acid by a variety of methods including ligation of adaptors and insertion of transposon sequences. In some such embodiments, a Y-adaptor may be ligated to at least one end of a target nucleic acid. The Y-adaptor can include a double-stranded sequence, and non-complementary strands, each strand comprising a different barcode. The target nucleic acid with ligated Y-adaptor can be amplified and sequenced such that each barcode can be used to identify the original sense or antisense strands. A similar method is described in Kinde I. et al., (2011) PNAS 108:9530-9535, the disclosure of which is incorporated herein by reference in its entirety. In some embodiments, the sense and antisense strands of a target nucleic acid are associated with a different barcode by inserting transposon sequences provided herein. In some such embodiments, the transposon sequences can comprise non-complementary barcodes.

Some embodiments of such methods include obtaining sequence information from a strand of a target double-stranded nucleic acid comprising (a) obtaining sequence data from a template nucleic acid comprising a first sequencing adapter and a second sequencing adapter having at least a portion of the double-stranded target nucleic acid disposed therebetween, wherein: (i) the first sequencing adapter comprises a double-stranded first barcode, a single-stranded first primer site and a single-stranded second primer site, wherein the first and second primer sites are non-complementary, and (ii) the second sequencing adapter comprising a double-stranded second barcode, a single-stranded third primer site and a single-stranded fourth primer site, wherein the third and fourth primer sites are non-complementary. In some embodiments, the first primer site of the sense strand of the template nucleic acid and the third primer site of the antisense sense strand of the template nucleic acid comprise the same sequence. In some embodiments, each barcode is different. In some embodiments, the first sequencing adapter comprises a single-stranded hairpin coupling the first primer site and second primer site.

In another embodiment, each end of a target nucleic acid is associated with an adaptor comprising a different barcode such that extension products from the sense and antisense strand of a nucleic acid can be distinguished from each other. In some embodiments, primer site sequences and barcodes are selected such that extension from a primer annealed to the sense strand yields products that can be distinguished from products of extension from a primer annealed to the antisense strand. In an example, the 3' sense primer site is the same as the 3' antisense primer site, but different from both the 5' sense and 5' antisense primer sites. Extension of primers annealed to the 3' sense primer site and the 3' antisense primer site would yield the following products from each strand:

Sense strand: (5') barcode 2-[target sequence]-barcode 1 (3')

Antisense strand: (5') barcode 1-[target sequence]-barcode 2 (3')

Thus, extension products from the sense and antisense strand of a nucleic acid can be distinguished from each other. An exemplary method is illustrated in Schmitt M. W., et al., PNAS (2012) 109:14508-13, the disclosure of which is incorporated herein by reference in its entirety. In some such methods, the barcodes and primers sites may be associated with the Target nucleic acid by a variety of methods including ligation of adaptors and insertion of transposon sequences. In some embodiments, transposon sequences can be designed to provide adaptors with hairpins. Hairpins provide the ability to maintain the physical contiguity of the sense and antisense strands of a target nucleic acid. A template nucleic acid can be prepared comprising hairpins using transposon sequences comprising linkers described herein. Examples of linkers include single-stranded nucleic acids.

Some embodiments of preparing a library of template nucleic acids for obtaining sequence information from each strand of a double-stranded target nucleic acid include (a) providing a population of transposomes comprising a transposase and a first transposon sequence comprising: (i) a first transposase recognition site, a first primer site, and a first barcode, and (ii) a second transposon sequence comprising a second transposase recognition site, a second primer site, and a second barcode, wherein the first transposon sequence is non-contiguous with the second transposon sequence; and (b) contacting the transposomes with a double-stranded nucleic acid under conditions such that said first and second transposon sequences insert into the double-stranded target nucleic acid, thereby preparing a library of template nucleic acids for obtaining sequence information from each strand of the double-stranded target nucleic acid. In some embodiments, the population of transposomes further comprises transposomes comprising a transposase and a transposon sequence comprising a third transposase recognition site and a fourth transposase recognition site having a barcode sequence disposed therebetween, said barcode sequence comprising a third barcode and a fourth barcode having a sequencing adapter disposed therebetween, said sequencing adapter comprising a third primer site and a fourth primer site having a linker disposed therebetween. In some embodiments, the first primer site of the sense strand of the template nucleic acid and the third primer site of the antisense sense strand of the template nucleic acid comprise the same sequence. Some embodiments also include a step (c) selecting for template nucleic acids comprising transposon sequences wherein the first transposon sequence is non-contiguous with the second transposon sequence and transposon sequences comprising a linker. In some embodiments, the linker comprises an affinity tag adapted to bind with a capture probe. In some embodiments, the affinity tag is selected from the group consisting of His, biotin, and streptavidin. In some embodiments, each barcode is different. In some embodiments, the linker comprises a single-stranded nucleic acid. In some embodiments, the target nucleic acid comprises genomic DNA.

Methods for Obtaining Haplotype Information

Some embodiments of the methods and compositions provided herein include methods of obtaining haplotype information from a target nucleic acid. Haplotype information can include determining the presence or absence of different sequences at specified loci in a target nucleic acid, such as a genome. For example, sequence information can be obtained for maternal and paternal copies of an allele. In a polyploid organism, sequence information can be obtained for at least one haplotype. Such methods are also useful in reducing the error rate in obtaining sequence information from target nucleic acid.

Generally, methods to obtain haplotype information include distributing a nucleic acid into one or more compartments such that each compartment comprises an amount of nucleic acid equivalent to about a haplotype of the nucleic acid, or equivalent to less than about a haplotype of the nucleic acid. Sequence information can then be obtained from each compartment, thereby obtaining haplotype information. Distributing the template nucleic acid into a plurality of vessels increases the probability that a single vessel includes a single copy of an allele or SNP, or that consensus sequence information obtained from a single vessel reflects the sequence information of an allele or SNP. As will be understood, in some such embodiments, a template nucleic acid may be diluted prior to compartmentalizing the template nucleic acid into a plurality of vessels. For example, each vessel can contain an amount of target nucleic acids equal to about a haplotype equivalent of the target nucleic acid. In some embodiments, a vessel can include less than about one haplotype equivalent of a target nucleic acid.

Methods of determining haplotype information, method of haplotyping with virtual compartments, methods of preparing target nucleic acids for haplotyping are described in WIPO publication WO/2014/142850, which is incorporated herein by reference.

EXAMPLES

Example 1—Maintaining Template Contiguity

This example illustrates a method for maintaining contiguity information of a template nucleic acid within a CE. The template nucleic acid is prepared using transposomes comprising non-contiguous transposon sequences in which Tn5 transposase stays bound to the template DNA post-transposition. The target nucleic acid is contacted with transposomes comprising Tn5 transposase, and non-contiguous transposon sequences. Samples which are further treated with SDS may appear as a smear of various fragments of template nucleic acid; samples not treated with SDS may show retention of putative high molecular weight template nucleic acid. Thus, even though a nucleic acid may be fragmented, adjacent sequences may still be associated with one another by the transposase.

In still another exemplary method, a library of template nucleic acids is prepared using transposomes comprising non-contiguous transposon sequences with target nucleic acid comprising human Chromosome. The CE comprises the target nucleic acid. Haplotype blocks up of DNA can be observed for samples in which transposase is removed by SDS post-dilution. Thus, by practicing methods as described herein target nucleic acids can maintain target integrity when transposed, be diluted, and be transformed into sequencing libraries.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

Example 2—Single Cell Whole Transcriptome Sequencing

This example describes a method for uniformly barcoding throughout the entire length of a cDNA and using the barcodes to determine the contiguity information of cDNA as well as to identify the cellular source, i.e. identify the single cell associated with the mRNA.

This example illustrates a method for sequencing the transcriptome of a single cell. In this example, droplet microfluidics is used to capture the transcriptome of multiple single cells on individual capture beads and contiguity preserving transposition and combinatorial indexing (CPT-seq) is then used to barcode the cDNA derived from the transcriptome of each single cell. In one embodiment, the method of the invention uses a multiple barcoding process to index single cell cDNA wherein a first barcode is added in a tagmentation reaction and a second barcode is added in a PCR amplification reaction.

In one example, poly-A+ RNA is captured from single cells and the captured poly-A+ RNA is processed in bulk for generation of a multiplexed sequencing library.

The method can include the following steps. At a step 1, RNA from a single cell is captured on a capture bead. For example, multiple single cells (e.g., about 1000 single cells) are encapsulated in individual droplets (i.e., on average, one cell and one bead per droplet) comprising a lysis buffer and a capture bead. Immobilized on the surface of the capture bead is a plurality of capture probes that include a poly-dT capture sequence and a PCR primer sequence. The lysis buffer composition of the droplet dissociates the single cell's cytoplasmic membrane releasing cytoplasmic RNA. The released poly-A+ RNA is captured by hybridization of the poly-A+ sequences on the RNA to the oligo-dT capture sequences immobilized on the surface of the co-encapsulated capture bead. Each capture bead now includes poly-A+ RNA from the transcriptome of a single cell. All poly-A+ RNA from a single cell is kept in proximity to one another on the capture bead.

At a step 2, capture beads with single-cell poly-A+ RNA thereon are pooled from multiple droplets (e.g., about 1000 capture beads) and double-stranded cDNA is synthesized. For example, the capture beads are pooled, washed, and first strand cDNA is synthesized using an RNAse H minus reverse transcriptase that is capable of strand switching. A strand switch primer is included during first strand cDNA synthesis allowing placement of a universal primer site at the 3' end of the cDNA. Double-stranded cDNA is then prepared using a universal primer and a high fidelity DNA polymerase in a PCR reaction (e.g., 1 to 2 cycles of PCR). Each capture bead now includes cDNA reverse transcribed from the poly-A+ RNA from a single cell.

At a step 3, capture beads with double-stranded cDNA thereon are distributed into wells of a 96-well plate such that there are about 10 capture beads per well.

At a step 4, double-stranded cDNA in each well is tagmented using 96 uniquely indexed transposomes. Tagmentation is used to modify the cDNA with adaptor and index sequences while preserving single-cell contiguity. Assembly of the 96 uniquely indexed transposome complexes used in the tagmentation reaction is described in more detail below. The tagmentation reaction adds the first part of a bipartite barcode to each future cDNA fragment. Each capture bead now includes tagmented cDNA from a single cell.

At a step 5, the capture beads in all wells are collected, pooled, washed, and redistributed into wells of another 96-well plate such that there are about 10 capture beads per well. The mRNA/cDNA from an individual cell stays on the surface of an individual bead and the transposase remains bound to the fragmented cDNA and keeps the fragments from dissociating.

At a step 6, transposase and tagmented cDNA are released from the capture beads. For example, an aliquot of an SDS (1% SDS) solution is added to each well to release bound transposase and tagmented cDNA from the capture beads.

At a step 7, tagmented cDNA in each well is amplified using PCR primers that include a P5 or P7 sequence and a unique barcode sequence. For example, one out of 96 unique combinations of barcoded P5 and P7 PCR primers is added to each well and the tagmented cDNA fragments are amplified. The PCR reaction adds the remaining portion of the bipartite barcode to each cDNA fragment. Each cDNA fragment now includes 4 barcode sequences: two sequences added in the tagmentation reaction and 2 sequences added during PCR amplification. Thus mRNA/cDNA from an individual cell is identified by the combination of the tagmentation index and the PCR index added through the amplification step.

At a step 8, the barcoded cDNA fragments from each well are pooled and sequenced.

In this example, 96×96 combinatorial indexing is used to barcode about 1000 single cells, with about a 5% chance of two cells having the same barcodes. Throughput can be readily scaled up by increasing the number of "compartments." For example, by using 384×384 combinatorial barcoding (about 147,456 virtual compartments), about 10,000 single cells can be individually barcoded in parallel with about a 3% chance of two cells having the same barcode.

This example also describes a process of assembling 96 unique barcoded transposome complexes for adding the first part of a bipartite barcode in a combinatorial barcoding protocol. The process includes, but is not limited to, the following steps.

In step A, 20 uniquely indexed transposons are formed by annealing individual indexed oligonucleotides, each containing the Tn5 Mosaic End (ME) sequence at their 3' end, to a universal 5' phosphorylated ME complementary oligonucleotide (pMENTS). For example, an indexed oligonucleotide 1110 that includes P5 sequences, a unique 8 base "i5" index sequence, a universal connector sequence Universal connector A-C15, and an ME sequence is annealed to a ME complementary sequence 1115. ME complimentary sequence 1115 is a universal 5' phosphorylated oligonucleotide (pMENTS) that is complementary to the ME sequences in indexed oligonucleotide 1110. Universal connector sequence A-C15 is used later to anneal custom index 2 sequencing primer.

A second set of annealing reactions (i.e., 12 individual annealing reactions) is performed to form a second set of 12 transposon that each include a unique 8 base "i7" index sequence adjacent to a P7 sequence. For example, an indexed oligonucleotide 1120 that includes P7 sequences, a unique 8 base i7 index sequence, a universal connector sequence B-D15 and an ME sequence is annealed to ME complementary sequence 1115. Universal connector sequence B-D15 is used later to anneal custom index 1 sequencing primer.

In step B, annealed P5_5 transposons 1125 (i.e., 8 P5_i5 transposons 1125 each with a unique 8 base i5 index sequence) and annealed P7_i7 transposons 1130 (i.e., 12 transposons 1130 each with a unique 8 base i7 index sequence) are assembled in individual reactions with Tn5 transposase to form transposome complexes. For example, each annealed P5_i5 transposon 1125 is incubated with Tn5 transposase 1135 at about 37° C. for about 1 hour to form a P5_i5 transposome complex 1140. Similarly, each annealed P7_i7 transposon 1130 is incubated with Tn5 transposase 1135 at about 37° C. for about 1 hour to form a P7_i7 transposome complex 1145.

In step C, 96 unique transposome complexes are made by combining aliquots of P5_i5 transposome complexes 1140 with aliquots of P7_i7 transposome complexes 1145. For example, P5_i5 transposome complexes 1140 are aliquoted in rows A through H of a 96-well plate and P7_i7 transposome complexes 1145 are aliquoted in columns 1 through 12 of the same 96-well plate. The combination of 8 P5_i5 transposome complexes 1140 and 12 P7_i7 transposome complexes 1145 creates 96 different index combinations.

To evaluate the assembled transposome complexes, a sequencing library from 10 single cells was prepared using a single tagmentation reaction and a single PCR reaction. Ten capture beads comprising cDNA from 10 single cells were pooled and tagmented using the P5_i5_1 plus P7_i7_1 transposome mix. The tagmented cDNA was then released from the capture beads and PCR amplified using barcoded P5 and P7 primers to generate a sequencing library. The fragment size distribution in the sequencing library was then analyzed using a Bioanalyzer. In some embodiments, clean up is performed after PCR. In some embodiments, the second SPRI clean up is performed after the first SPRI clean up. In some embodiments, the sample is diluted 10-fold before analyzing in a Bioanalyzer.

In another example, two different transposome complex mixes were used to prepare a sequencing library from 100 single cells. In this example, a split and pool protocol was used to evaluate the transposome complexes. One hundred capture beads comprising cDNA from 100 single cells were distributed into two tagmentation reactions, one tagmentation reaction was performed using the P5_i5_2 plus P7_i7_2 transposome mix and a second tagmentation reaction was performed using the P5_i5_3 plus P7_i7_3 transposome mix of. After the tagmentation reactions, the capture beads from each reaction were pooled and redistributed for PCR amplification using two unique combinations of barcoded P5 and P7 PCR primers (i.e., a first combination of P5 and P7 PCR primers and a second combination of P5 and P7 PCR primers) to generate two sequencing libraries. The fragment size distribution in each sequencing library was then analyzed using a Bioanalyzer. The barcoded library was analyzed after a single 0.7×SPRI clean-up step.

---

What is claimed is:

1. A method of analyzing at least two or more analytes of a plurality of single cells, the method comprising:
    (a) providing a plurality of contiguity preserving elements (CE), wherein each CE comprises a single cell;
    (b) lysing the single cells within the individual CE, wherein the analytes within the single cell are released within the individual CE;
    (c) providing a first reporter moiety to a first analyte within the single cell of each CE;
    (d) providing a second reporter moiety to a second analyte within the single cell of each CE, wherein the first analyte and the second analyte are different types of analytes;
    (e) modifying the analytes such that at least some of the first and second analytes of the individual CE comprise the first and second reporter moieties, respectively;
    (f) combining the individual CE comprising the analytes comprising the reporter moieties;
    (g) compartmentalizing the individual CE comprising the first and second analytes comprising the first and second reporter moieties, respectively into a plurality of compartments, wherein compartments comprise multiple individual CE;
    (h) providing a third reporter moiety to the first analyte comprising the first reporter moiety of each CE, wherein the third reporter moiety provided to the first analyte of each compartment is different from the third reporter moiety provided to the first analyte of each of the other compartments;
    (i) providing a fourth reporter moiety to the second analyte comprising the second reporter moiety of each CE, wherein the fourth reporter moiety provided to the second analyte of each compartment is different from the fourth reporter moiety provided to the second analyte of each of the other compartments;
    (j) further modifying the analytes such that at least some first analytes comprise the first and third reporter moieties and at least some second analytes comprise the second and fourth reporter moieties;
    (k) analyzing said analytes comprising the reporter moieties of each compartment, wherein such analysis detects the single cell which is the source of each analyte.

2. The method of claim 1, wherein the first and second reporter moieties identify the source of the analytes.

3. The method of claim 1, wherein the combination of the reporter moieties identifies the source of the analytes.

4. The method of claim 1, wherein detection of the analytes is done simultaneously.

5. The method of claim 1, wherein the first analyte is genomic DNA and the second analyte is cDNA.

6. The method of claim 5, wherein the modifying at least some of the genomic DNA and cDNA to comprise the first and second reporter moieties comprises contacting the genomic DNA and cDNA with a plurality of transposomes, each transposome comprising a transposase and a transposon sequence comprising the first reporter moiety or the second reporter moiety under conditions such that at least some of the transposon sequences are inserted into the genomic DNA and cDNA.

7. The method of claim 6, wherein step (g) further comprises removing the transposase from the genomic DNA and cDNA.

8. The method of claim 6, wherein first transposon sequences comprise a first primer site and second transposon sequences comprise a second primer site.

9. The method of claim 8, wherein the first primer site further comprises a first barcode and the second primer site further comprises a second barcode.

10. The method of claim 1, wherein the first, second, third, or fourth reporter moiety comprises a barcode.

11. The method of claim 1, wherein one analyte is protein.

12. The method of claim 1, wherein the first, second, third, or fourth reporter moieties comprise a primer binding site.

13. The method of claim 1, wherein the first, second, or both analytes are nucleic acids, and the analysis of the nucleic acid is by sequencing.

14. The method of claim 11, wherein the protein is labeled with a nucleic acid reporter moiety.

15. The method of claim 14, wherein the nucleic acid reporter moiety comprises a combinatorially derived set of barcodes.

16. The method of claim 13, wherein the nucleic acids comprising reporter moieties are amplified prior to analysis.

17. The method of claim 1, wherein the CE of step (a) comprises cells.

18. A method of analyzing at least two or more analytes of a plurality of single cells, the method comprising:
    (a) providing a plurality of contiguity preserving elements (CE), wherein each CE comprises cells;
    (b) providing a first reporter moiety to a first analyte within the cells of each CE;
    (c) providing a second reporter moiety to a second analyte within the cells of each CE, wherein the first analyte and the second analyte are different types of analytes;
    (d) modifying the analytes such that at least some of the first and second analytes of the individual CE comprise the first and second reporter moieties, respectively;
    (e) combining the individual CE comprising the analytes comprising the reporter moieties;
    (f) compartmentalizing the individual CE comprising the first and second analytes comprising the first and second reporter moieties, respectively into a plurality of compartments, wherein compartments comprise multiple individual CE;
    (g) providing a third reporter moiety to the first analyte comprising the first reporter moiety of each CE, wherein the third reporter moiety provided to the first analyte of each compartment is different from the third reporter moiety provided to the first analyte of each of the other compartments;
    (h) providing a fourth reporter moiety to the second analyte comprising the second reporter moiety of each CE, wherein the fourth reporter moiety provided to the second analyte of each compartment is different from the fourth reporter moiety provided to the second analyte of each of the other compartments;
    (i) further modifying the analytes such that at least some first analytes comprise the first and third reporter moieties and at least some second analytes comprise the second and fourth reporter moieties;
    (j) analyzing said analytes comprising the reporter moieties of each compartment, wherein such analysis detects the cell which is the source of each analyte.

19. The method of claim 18, wherein each CE of step (a) comprises a single cell.

20. The method of claim 1, wherein the plurality of CE comprises at least 1,000 CE.

21. The method of claim 18, wherein the plurality of CE comprises at least 1,000 CE.

22. The method of claim 1, wherein the cells of step (a) are embedded.

23. The method of claim 18, wherein the cells of step (a) are embedded.

* * * * *

SEQUENCE LISTING

```
<160> NUMBER OF SEQ ID NOS: 3

<210> SEQ ID NO 1
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
aatgatacgg cgaccaccga gatctacac                                    29

<210> SEQ ID NO 2
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
caagcagaag acggcatacg agat                                         24

<210> SEQ ID NO 3
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aaaaaaaaaa                                                         10
```